US008912355B2

(12) United States Patent
Pandey et al.

(10) Patent No.: US 8,912,355 B2
(45) Date of Patent: Dec. 16, 2014

(54) LINOLEIC PHOSPHOLIPIDS AND USES THEREOF FOR INHIBITING INFLAMMATORY AND NEURODEGENERATIVE PROCESSES

(75) Inventors: Nihar Pandey, Ottawa (CA); Daniel Sparks, Gatineau (CA)

(73) Assignee: University of Ottawa Heart Institute, Ottawa, Ontario (CA)

(*) Notice: Subject to any disclaimer, the term of this patent is extended or adjusted under 35 U.S.C. 154(b) by 251 days.

(21) Appl. No.: 12/892,671

(22) Filed: Sep. 28, 2010

(65) Prior Publication Data
US 2011/0077224 A1 Mar. 31, 2011

Related U.S. Application Data

(60) Provisional application No. 61/246,775, filed on Sep. 29, 2009.

(51) Int. Cl.
A61K 31/661 (2006.01)
A61P 25/28 (2006.01)
A61P 29/00 (2006.01)
C07F 9/10 (2006.01)

(52) U.S. Cl.
CPC ............... *C07F 9/10* (2013.01); *A61K 31/661* (2013.01)
USPC ............................ 558/180; 514/121; 435/375

(58) Field of Classification Search
CPC ................................. C07F 9/10; A61K 31/661
USPC ................. 435/375; 514/121, 77; 558/180; 554/480
See application file for complete search history.

(56) References Cited

FOREIGN PATENT DOCUMENTS

WO WO2008014084 * 9/2008 ............ A61K 31/685
WO WO2008106772 * 9/2008 ............ A61K 31/685

OTHER PUBLICATIONS

Treede et al. (The journal of biological chemistry, vol. 282, No. 37, pp. 27155-27164.*
Ross (New England Journal of Medicine, 1999, vol. 340, No. 2, pp. 115-126.*
Casserly et al. (Lancet 2004; 363: pp. 1139-1146).*
Ong et al. (Ann. N.Y. Acad. Sci. 1012: pp. 51-64 (2004).*
Selkoe, D. J., "Alzheimer's Disease: Genes, Proteins, and Therapy", Physiol. Rev., vol. 81, No. 2, pp. 741-766 (2001).
McGeer, P. L. et al., "Arthritis and Anti-Inflammatory Agents as Possible Protective Factors for Alzheimer's Disease: a Review of 17 Epidemiologic Studies", Amer. Academy of Neurology, vol. 47, pp. 425-432 (1996).
Kalaria, R. N., (http://ovidsp.tx.ovid.com/sp-3.4.1a/ovidweb.cgi) "Microglia and Alzheimer's Disease", Curr. Opin. In Hematol., vol. 6, No. 1, pp. 15-24 (1999).
Akiyama, H., et al., "Inflammation and Alzheimer's Disease", Neurobiol. of Aging, vol. 21, pp. 383-421 (2000).
Paris, D., et al., "Inhibition of Aβ Production by NF-κB Inhibitors", Neurosci. Lett., vol. 415, pp. 11-16 (2007).
Bales, K. R. et al., "The NF-κB/Rel Family of Proteins Mediates Aβ-Induced Neurotoxicity and Glial Activation", Molecular Brain Res., vol. 57, pp. 63-72 (1998).

(Continued)

*Primary Examiner* — Savitha Rao
(74) *Attorney, Agent, or Firm* — Winston & Strawn LLP

(57) ABSTRACT

Described herein are compositions of an linoleic phospholipid for inhibiting inflammatory pathways or neurodegenerative processes. Also provided are uses of such compositions and methods of inhibiting inflammatory or neurodegenerative processes by administering a composition that includes an linoleic phospholipid and optionally a carrier to a cell, cell culture or subject in need of such treatment.

4 Claims, 13 Drawing Sheets

(56) References Cited

OTHER PUBLICATIONS

Sung, S., et al., "Modulation of Nuclear Factor-κB Activity by Indomethacin Influences Aβ Levels but not Aβ Precursor Protein Metabolism in a Model of Alzheimer's Disease", Am. J. Pathol., vol. 165, No. 6, pp. 2197-2206 (2004).
Pandey, N. R. et al., "Linoleic Acid-Enriched Phospholipids Act through Peroxisome Proliferator-Activated Receptors α to Stimulate Hepatic Apolipoprotein A-I Secretion", Biochemistry, vol. 47, pp. 1579-1587 (2008).
Pandey, N. R. et al., "Phospholipids as Cardiovascular Therapeutics", Curr. Opin. Investig. Drugs. vol. 9, No. 3 pp. 281-285 (2008).
Barter, P. et al., "High Density Lipoproteins (HDLs) and Atherosclerosis; the Unanswered Questions", Atherosclerosis, vol. 168, pp. 195-211 (2003).
Barter, P. J. et al., "New Insights into the Role of HDL as an Anti-Inflammatory Agent in the Prevention of Cardiovascular Disease", Curr. Cardiology Reports, vol. 9, pp. 493-498 (2007).
Thoenes, M. et al., "The Effects of Extended-Release Niacin on Carotid Intimal Media Thickness, Endothelial Function and Inflammatory Markers in Patients with the Metabolic Syndrome", Int. J. of Clin. Pract., vol. 61, No. 11, pp. 1942-1948 (2007).
Kuvin, J. T. et al. "Effects of Extended-Release Niacin on Lipoprotein Particle Size, Distribution, and Inflammatory Markers in Patients with Coronary Artery Disease", Am. J. Cardiol., vol. 98, pp. 743-745 (2006).
Cao, Q. et al., "Dilinoleoylphosphatidylcholine Decreases LPS-Induced TNF-α Generation in Kupffer Cells of Ethanol-Fed Rats: Respective Roles of MAPKs and NF-κB", Biochem. and Biophys. Res. Commun., vol. 294, pp. 849-853 (2002).
Cao, Q. et al., "Dilinoleoylphosphatidylcholine Decreases Acetaldehyde-induced TNF-α Generation in Kupffer Cells of Ethanol-Fed Rats", Biochem. And Biophys. Res. Commun. vol. 299, 459-464 (2002).
Oneta, C. M. et al., "Dilinoleoylphosphatidylcholine Selectively Modulates Lipopolysaccharide-Induced Kupffer Cell Activation", J. Lab Clin. Med., vol. 134, pp. 466-470 (1999).
Treede, I. et al., "Anti-inflammatory Effects of Phosphatidylcholine", J. Biol. Chem., vol. 282, No. 37, pp. 27155-27164 (2007).
Little, A. et al., "A Double-Blind, Placebo Controlled Trial of High-Dose Lecithin in Alzheimer's Disease", J. of Neurol., Neurosurg. and Psychiatry, vol. 48, pp. 736-742 (1985).
Higgins, J. P. et al., "Lecithin for Dementia and Cognitive Impairment", The Cochrane Library, Issue 1 (2009).
Engel, R. R. et al., "Double-Blind Cross-Over Study of Phosphatidylserine vs. Placebo in Patients with Early Dementia of the Alzheimer Type", Eur. Neuropsychopharmacol., vol. 2, pp. 149-155 (1992).
Hopewell, S. et al. "Phosphatidylinositol Acts Through Mitogen-Activated Protein Kinase to Stimulate Hepatic Apolipoprotein A-I Secretion", Metabolism Clin. and Exper., vol. 57, pp. 1677-1684 (2008).
Wilson, T. A. et al. "Soy Lecithin Reduces Plasma Lipoprotein Cholesterol and Early Atherogenesis in Hypercholesterolemic Monkeys and Hamsters: Beyond Linoleate", Atherosclerosis, vol. 140, pp. 147-153 (1998).
Lieber, C. S., "Alcoholic Liver Disease: New Insights in Pathogenesis Lead to New Treatments", J. of Hepatol., vol. 32, pp. 113-128 (2000).
Lieber, C. S., "Pathogenesis and Treatment of Alcoholic Liver Disease: Progress Over the Last 50 Years", Rocz. Akad. Med. Bialymst., vol. 50, pp. 7-20 (2005).
Stremmel, W. et al., "Retarded Release Phosphatidylcholine Benefits Patients with Chronic Active Ulcerative Colitis", Gut., vol. 54, pp. 966-971 (2005).
Chung, S. Y. et al., "Administration of Phosphatidylcholine Increases Brain Acetylcholine Concentration and Improves Memory in Mice with Dementia", J. of Nutr., vol. 125, No. 6, pp. 1484-1489 (1995).
Suzuki, S., et al., "Oral Administration of Soybean Lecithin Transphosphatidylated Phosphatidylserine Improves Memory Impairment in Aged Rats", J. of Nutr., vol. 131, No. 11, pp. 2951-2956 (2001).
Burgess, J. W. et al., "Phosphatidylinositol Increases HDL-C Levels in Humans", J. Lipid Res., vol. 46, pp. 350-355 (2005).
Merched, A. et al. "Decreased High-Density Lipoprotein Cholesterol and Serum Apolipoprotein AI Concentrations are Highly Correlated with the Severity of Alzheimer's Disease", Neurobiol. of Aging, vol. 21, pp. 27-30 (2000).
Morris, M. C. et al., "Dietary Niacin and the Risk of Incident Alzheimer's Disease and of Cognitive Decline", J. of Neurol., Neurosurg. and Psychiatry, vol. 75, pp. 1093-1099 (2004).
Jang, J. H. et al., "β-Amyloid-Induced Apoptosis is Associated with Cyclooxygenase-2 Up-Regulation Via the Mitogen-Activated Protein Kinase-NF-κB Signaling Pathway", Free Radic. Biol. and Med., vol. 38, pp. 1604-1613 (2005).
Lecureur, V. et al., "ERK-Dependent Induction of TNFα Expression by the Environmental Contaminant Benzo(a)pyrene in Primary Human Macrophages", FEBS Lett., vol. 579, pp. 1904-1910 (2005).
Wu, D. et al. "Cytochrome P4502E1 Sensitizes to Tumor Necrosis Factor Alpha-Induced Liver Injury through Activation of Mitogen-Activated Protein Kinases in Mice", Hepatology, vol. 47, pp. 1005-1017 (2008).
Duncia, J. V. et al. "MEK Inhibitors: the Chemistry and Biological Activity of U0126, its Analogs, and Cyclization Products", Bioorg. & Med. Chem. Letters., vol. 8, pp. 2839-2844 (1998).
Mak, K. M. et al. "Dilinoleoylphosphatidylcholine Reproduces the Antiapoptotic Actions of Polyenylphosphatidylcholine against Ethanol-Induced Hepatocyte Apoptosis", Alcohol.: Clin. and Exp. Res., vol. 27, No. 6, 997-1005 (2003).
Goedert, M. et al. "Neurofibrillary Tangles and β-Amyloid Deposits in Alzheimer's Disease", Curr. Opin. Neurobiol, vol. 1, pp. 441-447 (1991).
Goedert, M. et al., "Tau Proteins and Neurofibrillary Degeneration", Brain Pathol., vol. 1, pp. 279-286 (1991).
Guise, S. et al. "Hyperphosphorylation of Tau is Mediated by ERK Activation during Anticancer Drug-Induced Apoptosis in Neuroblastoma Cells", J. Neurosci, Res., vol. 63, pp. 257-267 (2001).
Gómez-Ramos, A. et al., "Tau Phosphorylation and Assembly", Acta Neurobiol. Exp., vol. 64, pp. 33-39 (2004).
Kayed, R. et al. "Common Structure of Soluble Amyloid Oligomers Implies Common Mechanism of Pathogenesis", Science, vol. 300, pp. 486-489 (2003).
Shankar, G. M. et al. "Amyloid-Beta Protein Dimers Isolated Directly from Alzheirner's Brains Impair Synaptic Plasticity and Memory", Nat. Med., vol. 14, No. 8, pp. 837-842 (2008).
Irvine, G. B. et al. "Protein Aggregation in the Brain: the Molecular Basis for Alzheimer's and Parkinson's Diseases", Mol. Med., vol. 14, pp. 451-464 (2008).
Furukawa, K. et al. "Increased Activity-Regulating and Neuroprotective Efficacy of α-Secretase-Derived Secreted Amyloid Precursor Protein Conferred by a C-Terminal Heparin-Binding Domain", J. of Neurochem., vol. 67, pp. 1882-1896 (1996).
Combs, C. K. et al., "β-Amyloid Stimulation of Microglia and Monocytes Results in TNFα-Dependent Expression of Inducible Nitric Oxide Synthase and Neuronal Apoptosis", J. of Neurosci., vol. 21, No. 4, pp. 1179-1188 (2001).
Combs, C. K. et al. "Regulation of β-Amyloid Stimulated Proinflammatory Responses by Peroxisome Proliferator-Activated Receptor α", Neurochem. Int., vol. 39, pp. 449-457 (2001).
Walsh, D. M. et al. "The Role of Cell-Derived Oligomers of Aβ in Alzheirner's Disease and Avenues for Therapeutic Intervention", Biochern. Soc. Trans., vol. 33, pp. 1087-1090 (2005).
Yin, Y. I. et al. "γ-Secretase Substrate Concentration Modulates the Aβ42/Aβ40 Ratio: Implications for Alzheimer Disease", J. Biol. Chem, vol. 282, No. 32., pp. 23639-23644 (2007).
Farooqui, A. A. et al. "Biochemical Aspects of Neurodegeneration in Human Brain: Involvement of Neural Membrane Phospholipids and Phospholipases $A_2$", Neurochem. Res., vol. 29, No. 11, pp. 1961-1977 (2004).
Bazan, N. G., "Synaptic Signaling by Lipids in the Life and Death of Neurons", Mol. Neurobiol., vol. 31, pp. 219-230 (2005).

(56) References Cited

OTHER PUBLICATIONS

Söderberg, M. et al., "Fatty Acid Composition of Brain Phospholipids in Aging and in Alzheimer's Disease", Lipids, vol. 26, pp. 421-425 (1991).
Nitsch, R. M. et al., "Evidence for a Membrane Defect in Alzheimer Disease Brain", Proc. Natl. Acad. Sci. USA, vol. 89, pp. 1671-1675 (1992).
Wells, K. et al., "Neural Membrane Phospholipids in Alzheimer Disease", Neurochem. Res., vol. 20, No. 20, pp. 1329-1333 (1995).
Pettegrew, J. W. et al., "Brain Membrane Phospholipid Alterations in Alzheimer's Disease", Neurochem. Res., vol. 26, No. 7, pp. 771-782 (2001).
Connor, W. E. et al., "Dietary Effects on Brain Fatty Acid Composition: The Reversibility of N-3 Fatty Acid Deficiency and Turnover of Docosahexaenoic Acid in the Brain, Erythrocytes, and Plasma of Rhesus Monkeys", J. Lipid Res., vol. 31, pp. 237-247 (1990).
Fenton, W. S. et al., "Essential Fatty Acids, Lipid Membrane Abnormalities, and the Diagnosis and Treatment of Schizophrenia", Biol., Psychiatry, vol. 47, pp. 8-21 (2000).
Sumiyoshi, T. et al., "Essential Polyunsaturated Fatty Acids and Social Cognition in Schizophrenia", Psychiatry Res., vol. 157, pp. 87-93 (2008).

\* cited by examiner

LINOLEIC PHOSPHOLIPIDS AND USES THEREOF FOR INHIBITING INFLAMMATORY AND NEURODEGENERATIVE PROCESSES

This application claims the benefit of application No. 61/246,775 filed Sep. 29, 2009, the entire content of which is expressly incorporated herein by reference thereto.

FIELD OF INVENTION

The present invention relates to phospholipid compositions and uses thereof.

BACKGROUND OF THE INVENTION

Neurodegeneration in Alzheimer's disease (AD) is associated with the accumulation of extracellular plaques of small peptides, called amyloid-β (Aβ), and intracellular neurofibrillary tangles, comprising aggregates of hyperphosphorylated tau protein (1). Evidence suggests that inflammatory events are involved in the pathogenesis of AD. Pro-inflammatory molecules are present at sites of Aβ plaques and anti-inflammatory drugs slow the progression of the disease (2-4).

Cells of the brain respond to ischemia and increased concentrations of Aβ by generating pro-inflammatory mediators, such as TNFα, 1β, and prostanglandins. The production of these inflammatory factors is regulated by nuclear factor kappa B (NF-κB), a transcription factor that is widely expressed in the nervous system. NF-κB immunoreactivity is elevated in regions of neuronal plaques in AD patients, suggesting that NF-κB pathways may be activated in AD brains (5). Aβ peptides have been shown to activate NF-κB in primary neurons and astrocytes (6). Studies have shown that anti-inflammatory drugs, such as indomethacin, can reduce the level of Aβ peptides and NF-κB in the brains of the transgenic mouse model of AD (TG2576) (7). Cell culture systems further suggest that a wide array of NF-κB inhibitors may be able to block the formation of Aβ(5). NF-κB inhibitors are therefore believed to have therapeutic importance in the treatment of AD patients, by both blocking inflammatory processes and the formation of Aβ.

Linoleic acid phospholipids, such as dilinoleoylphosphatidylcholine (DLPC), have been shown to regulate the hepatic production of HDL, through effects on mitogen-activated protein kinase (MAPK) and PPARα(8,9). An inverse relationship between inflammation and plasma HDL levels has long been recognized (10,11) and studies suggest that some HDL therapeutics may directly act as anti-inflammatory compounds (12,13). DLPC directly reduces alcohol-induced hepatic inflammatory cascades in experimental animal and cellular models (14-16) and studies show that PC can also inhibit TNF-α-induced inflammatory responses in model human intestinal cells, CaCO-2 (17).

Phospholipids (PL) are important components of the human body and constituents of the circulating plasma lipoproteins. PL have been suggested to have therapeutic value in treating inflammatory and neurodegenerative diseases (18, 19,26,27). PL have been shown to have anti-inflammatory effects in both the liver and intestinal track (17,28). PL protect against alcoholic liver injury (14,27,28) and have also been shown to be effective at alleviating gastrointestinal inflammation caused by ulcerative colitis (29). Other studies have shown therapeutic value of PL for both Alzheimer's Disease (AD) and other neurological diseases (18,19). PL have shown the potential to improve memory and cognitive function in rodents (30-32) and PL have also been used for treating senile dementia and other neurodegenerative disorders in humans (20-24).

The inventors have previously shown that the acyl chain composition of PL directly impact cellular signaling and transcriptional processes (8,9). Soy PL are enriched in the linoleic fatty acid, linoleic acid, an 18 carbon acyl chain with 2 unsaturations (18:2). Linoleic PL act through MAPK and PPARα pathways to stimulate hepatic HDL/apoA-I secretion and raise plasma HDL levels (8,9,33). Decreased plasma HDL and apoA-I levels are highly correlated with the severity of AD (34,35). Niacin also acts through MAPK and PPARα and has been shown to have both HDL raising therapeutic value as well as anti-inflammatory properties (12,13). Dietary niacin may also directly protect against AD and age related cognitive decline (36).

There is a need in the art for novel anti-inflammatory compositions. Further, there is a need in the art for novel compositions comprising linoleic phospholipids. Also, there is a need in the art for novel methods and for inhibiting inflammatory pathways and/or neurodegenerative processes.

SUMMARY OF THE INVENTION

In an embodiment of the present invention, there is provided a composition comprising a linoleic phospholipid for inhibiting inflammatory or neurodegenerative processes.

Also provided is a composition as described above, wherein the linoleic phospholipid is DLPC.

The present invention also provides a composition as described above, wherein the composition is an oral dosage formulation. Preferably, the oral dosage formulation comprises a gastrointestinal protectant. In one embodiment, the gastrointestinal protectant is an enteric coating. In a further embodiment, the gastrointestinal protectant is a pH stabilizer. Other gastrointestinal protectants are also contemplated.

The present invention also contemplates a method of inhibiting inflammatory and/or neurodegenerative processes comprising administering a composition comprising a linoleic phospholipid to a cell, cell culture, tissue or subject in need of such treatment. The method may be an in-vitro method or in-vivo method. An in-vivo method is preferred.

The present invention also provides a method as described above, wherein the linoleic phospholipid is DLPC.

The present invention also contemplates a method of inhibiting NF-kB pathways, blocking amyloid-beta expression, blocking tau hyperphosphorylation, or a combination thereof, comprising administering a composition comprising a linoleic phospholipid to a subject in need thereof. In a preferred embodiment, the linoleic phospholipid is DLPC in an oral dosage formulation comprising a gastrointestinal protectant.

Other additional aspects of the invention are described herein.

BRIEF DESCRIPTION OF THE DRAWINGS

These and other features of the invention will become more apparent from the following description in which reference is made to the appended drawings wherein.

DETAILED DESCRIPTION OF THE INVENTION

Figure 1:
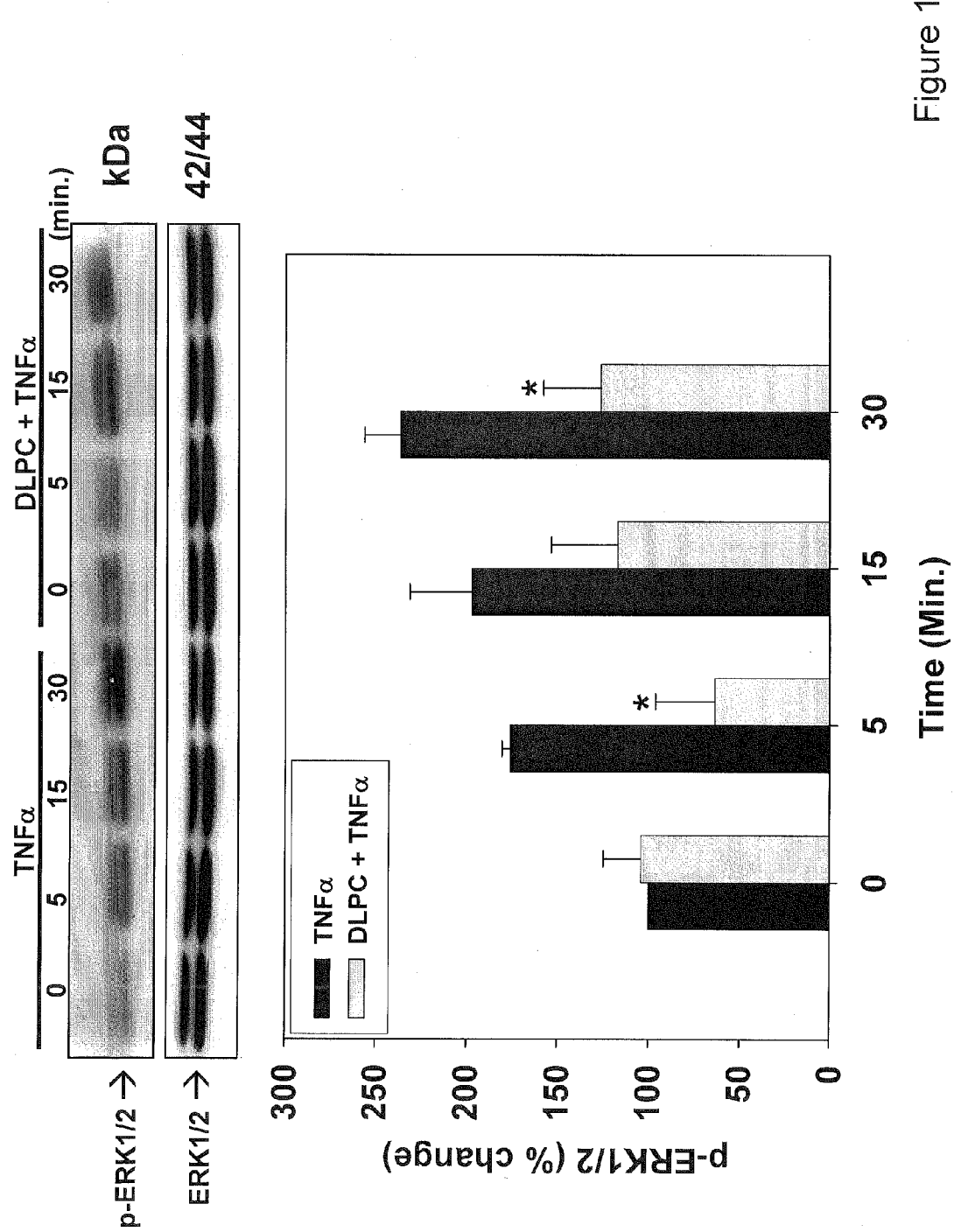
FIG. 1 shows that DLPC blocks ERK1/2 phosphorylation. Pre-confluent SH-SY5Y cells were pre-incubated with 12 μM DLPC for 30 min. and then incubated with TNFα (10 ng/ml) for the indicated times. Phospho and total ERK1/2 expression were analyzed by Western blotting. Histograms representing densitometry analysis of phospho ERK1/2 and the values are presented relative to total ERK1/2 control and are expressed as mean±SEM of at least 3 independent experiments. *P<0.05 vs. TNFα alone.

The following description is of a preferred embodiment.

According to the present invention there is provided a composition comprising linoleic phospholipids. Preferably, the composition comprises linoleic acid phospholipids such as, but not limited to, dilinoleoylphosphatidylcholine (DLPC). In a preferred embodiment, which is not meant to be limiting in any manner, the composition comprises DLPC.

It is also contemplated that the composition may comprise one or more additional components, for example, an aqueous component such as water or a buffer, a non-aqueous component, such as, dimethylsulfoxide, ethanol or the like, or a combination of an aqueous component and a non-aqueous component. Other components may also be present.

In a preferred embodiment, the linoleic phospholipid or composition comprising same further comprises a gastrointestinal protectant such as, $H_1$ blockers, $H_2$ blockers, beta-adrenergic agonists, and combinations thereof, or of otastat potassium or one or more other compounds that provide GI-protection. As phospholipids are degraded in the stomach by a low pH, use of pH protection strategies, for example, an enteric coating or the like as would be known in the art, would therefore be expected to increase the bioavailability and efficacy of the compound following administration.

In a further embodiment, the composition as described herein may include one or more pharmaceutically acceptable carriers, and optionally any other therapeutic ingredients, stabilizers, or the like. The compositions of the invention as described herein may also include polymeric excipients/additives or carriers, for example, but not limited to polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (for example, but not limited to cyclodextrins, such as 2-hydroxypropyl-cyclodextrin and sulfobutylether-cyclodextrin), polyethylene glycols, and pectin. The compositions may further include diluents, buffers, binders, disintegrants, thickeners, lubricants, preservatives, antioxidants, flavoring agents, taste-masking agents, inorganic salts (for example, but not limited to sodium chloride, potassium chloride or the like), antimicrobial agents (for example, but not limited to benzalkonium chloride), sweeteners, antistatic agents, surfactants (for example, but not limited to polysorbates such as TWEEN 20, 80, and pluronics such as F68 and F88), sorbitan esters, other lipids (for example, but not limited to phospholipids such as lecithin and other phosphatidylcholines, phosphatidylethanolamines, fatty acids and fatty esters), steroids (for example, but not limited to cholesterol), and chelating agents (for example, but not limited to EDTA, zinc and other such suitable cations). Other pharmaceutical excipients and/or additives suitable for use in the compositions according to the invention may be obtained from "Remington: The Science & Practice of Pharmacy", 19th ed., Williams & Williams, (1995), and in the Physician's Desk Reference, 52nd ed., Medical Economics, Montvale, N.J. (1998), and in Handbook of Pharmaceutical Excipients, Third Ed., Ed. A. H. Kibbe, Pharmaceutical Press, 2000, all of which are herein incorporated by reference in their entirety.

The composition as described herein is preferably formulated for oral administration, although other forms of administration are contemplated. The compositions may be presented in unit dosage form and may be prepared by any of the methods well known in the art of pharmacy. In a preferred embodiment, the dosage form is a tablet or capsule.

The results provided herein indicate that DLPC can block neuronal inflammatory cascades and prevent potential pathological consequences in the neuronal metabolism of amyloid and tau proteins. Specifically, tumor necrosis factor (TNFα) and $H_2O_2$ activate mitogen-activated protein kinase (MAPK) in SH-SY5Y cells within 5 min and this activation is blocked by DLPC (12 µM). DLPC blocks IκBα phosphorylation and degradation in the SH-SY5Y cells and prevents the phosphorylation and activation of nuclear factor-kappa B (NF-κB). DLPC blocks induction of MAPK and NF-κB in similar fashion to the MAPK-inhibitor, U0126 (10 µM). DLPC blocks TNFα, $H_2O_2$ and lipopolysaccepide (LPS)-induced neuronal tau phosphorylation. Cellular amyloid precursor protein levels are reduced by DLPC and LPS-induced amyloid beta (1-42) expression and secretion in SH-SY5Y cells are blocked by DLPC.

The present invention also describes the utility of linoleic acid phospholipids (PL) to prevent and/or treat neurodegenerative disease by one or more of inhibiting NF-kB-dependent inflammatory pathways, blocking amyloid-beta expression, blocking tau hyperphosphorylation, or a combination thereof. Demonstrated herein is the inhibition of nuclear factor kappa B with PL to prevent neurodegenerative events in a human neuronal cell line by blocking the abnormal metabolism of both amyloid and tau proteins. Thus PL is expected to have therapeutic utility for treating human neurodegenerative disease.

Based on the results obtained herein, the compositions as described herein may be employed in the prevention, delay of onset, or treatment of inflammatory and neurodegenerative diseases or disorders such as, but not limited to Alzheimer's Disease.

In a further embodiment, the compositions as described herein may be employed to inhibit inflammatory pathways and neurodegenerative processes. Methods of inhibiting inflammatory pathways and neurodegenerative processes may be performed in-vitro or in-vivo.

The present invention also contemplates a method of inhibiting NF-κB, Tau phosphorylation, amyloid-β secretion or any combination thereof comprising the step of administering a composition comprising linoleic phospholipids, preferably DLPC to one or more cells, a cell culture, tissue or a subject to inhibit NF-κB, Tau phosphorylation, amyloid-β secretion, or a combination thereof.

The present invention also contemplates a method to prevent or treat NF-κB, Tau, and/or amyloid-β associated diseases or disorders comprising administering a composition comprising linoleic phospholipids, preferably DLPC to a subject having a NF-κB, Tau, and/or amyloid-β associated diseases or disorders in order to prevent and/or treat the disease or disorder.

The present invention also contemplates a method as described above wherein the subject is first diagnosed with a NF-κB, Tau, and/or amyloid-β associated disease or disorder.

The present invention also contemplates the use of DLPC to reduce levels of phosphorylated tau protein in vitro or in vivo. In a further embodiment, the present invention provides a method for inhibiting the normal phosphorylation state of Tau protein.

The present invention also contemplates the use of DLPC to reduce levels of amyloid β peptide and secretion in vitro or in vivo. In a further embodiment, there is provided a method of inhibiting the production of amyloidosis in a subject.

The present invention will be further illustrated in the following examples.

EXAMPLES

Materials and Methods

Chemicals—Dilinoeoylphosphatidylcholine (DLPC) was obtained from Avanti Polar Lipids Inc., Alabaster, Ala. The MEK1/2 inhibitor, UO126, and its inactive isoform, U0124, were purchased from Calbiochem (La Jolla, Calif.). Lipopolysacharide (LPS) and $H_2O_2$ were from Sigma Chemical Co. Anti-human hyper-phosphorylated tau (paired helical filament-PHF) clone-AT8 antibody (Cat # MN1020) doubly phosphorylated at Ser202/Thr205 was procured from Thermo Scientific (Rockford, Ill., USA). Total tau-B11E8 antibody (Cat # sc58855) and donkey anti-goat IgG-HRP (cat# sc-2020) were from Santa Cruz Biotechnology (Santa Cruz, Calif., USA). Amyloid beta (Aβ1-42) antibody (Cat # ab 17905-50) was from Abcam and amyloid precursor protein (APP-N terminus; Cat # A8967) antibody was from Sigma-Aldrich, Inc. (St. Louis, Mo., USA). Phospho-NF-κB p65 (Cat #3036), NF-κB p65 (Cat #3034), phospho-IκNα (Cat #9246), IκBα (Cat #9242), phospho MAPK-ERK1/2 (Cat #9101), ERK1/2 (Cat #9102), total anti-β-actin (cat #4967) and anti-rabbit IgG-HRP (cat #7074) were obtained from Cell Signaling Technology, Danvers, Mass. Affinity purified peroxidase linked goat anti-mouse antibody (cat#4741806) was purchased from Kirkengaard and Perry Labs. Unless otherwise stated, drugs and inhibitors were of analytical grade and were solubilized in dimethyl sulfoxide (DMSO). All chemical inhibitors were used at reported IC50 concentrations to block various signaling pathways.

Cells and Cell Culture—Human neuroblastoma (SH-SY5Y) cells were obtained from American Type Cell Culture (ATCC Number CRL-2266; Manassas, Va., USA). SH-SY5Y was cultured and maintained in F12:DMEM (1:1, v/v) media condition with 10% FBS and 1% penicillin/streptomycin in a 37° C./5% $CO_2$ exchange condition. Passages 3-10 were used in the present study and confluent cells were subjected to stimulation with drugs for indicated times under serum-starved conditions.

Preparation of Phospholipid Vesicles—Phospholipid Vesicles in Phosphate-Buffered saline (PBS; 1 mg/mL) were prepared by sonication as previously described (8). Briefly, pure dilinoeoylphosphatidylcholine (DLPC) in chloroform was dried down under $N_2$ and 1 mL of PBS was added by vortexing. The mix was then sonicated (Branson sonicator set at 100% duty cycle and 10% power) for 1 min. The sonicated preparation was incubated for 30 min at 37° C. in a water bath, and samples were resonicated for 5 min at 95% duty cycle and 10% power and filtered before use.

Western Blot Analysis—After incubation with drugs for the indicated times and doses, cells were washed twice with ice-cold PBS-T on ice. Cells were lysed by adding buffer [NaF 1 mmol/L, NaCl 5 mmol/L, EDTA 1 mmol/L, NP40 1 mmol/L (Roche Diagnostics, Indianapolis, Ind.), HEPES 10 mmol/L, pepstatin A 1 mg/mL, leupeptin 1 mg/mL, aprotinin 1 mg/mL, $Na_3VO_4$ 1 mmol/L, and PMSF 1 mmol/L] and total protein was extracted. An equal amount of cell proteins were separated by 12% SDS-PAGE and were analyzed by Western blot using specific antibodies to TNFα, Aβ, APP, phospho-ERK1/2, ERK1/2, phospho-tau, tau, phospho-IκBα, IκBα, phospho-NF-κB and NF-κB. Blots for the similar experiments were also subjected to β-actin for a loading control. Band intensity was analyzed with the Alpha-Innotech Fluor Chem™ HD Imager.

Aβ quantification—Aβ immuno-quantification was performed in conditioned media after incubation with the inhibitors/agonists and/or phospholipids for the indicated times and doses. Briefly, the conditioned media was removed and briefly centrifuged to remove any cells. Equal amount (30 μL) of 1:1 dilution of conditioned media in Laemmli's sample buffer containing β-mercaptoethanol was separated by 12% SDS-PAGE. The proteins were transferred onto a PVDF membrane and probed using specific antibody for Aβ and IgG linked HRP secondary antibody in 5% Milk/TBST. Blots were developed using the West Femto Maximum Sensitivity Substrate (Pierce, Rockford, Ill.) on the Fluorochem AlphaImager. Band intensities were analyzed using the Spot-densitometer application of the AlphaEaseFC software and values were corrected with total cell proteins in cell lysates. The cells were washed twice with ice-cold PBS on ice and then lysed with NP40 lysis buffer (Biosource, Camarillo, Calif.) [50 mM Tris, pH 7.4, 250 mM NaCl, 5 mM EDTA, 50 mM NaF, 1 mM $Na_3VO_4$, 1% NP40 and 0.02% $NaN_3$] supplemented with 1 mM PMSF and 1× protease inhibitor cocktail (Sigma, Saint Louis, Mo.) [AEBSF, aprotinin, bestatin hydrochloride, E-64, EDTA and leupeptin hemisulfate salt]. Total protein concentration was determined using the BCA protein assay (Pierce, Rockford, Ill.) in cell lysate. Aβ western blots were performed in total cell lysates.

Statistical Analysis—Values are shown as Mean±SEM for at least 3 independent experiments and $P<0.05$ was considered significant. Differences between mean values were evaluated by one-way analysis of variance (ANOVA) on ranks by a pairwise multiple comparison using the Student-Newman-Keuls post-hoc test (SigmaStat; Systat Software, Inc., San Jose, Calif.).

Example 1

DLPC Blocks ERK Phosphorylation in SH-SY5Y Cells

Previous studies showed that linoleic phospholipids act through the mitogen-activated protein kinase (MAPK) pathway (8,25). Experiments were undertaken to determine if DLPC can block a tumor necrosis factor (TNFα) activation of MAPK in neuroblastoma cells. SH-SY5Y cells were treated with DLPC (12 μM) and/or TNFα (10 ng/ml) and ERK 1/2 phosphorylation was quantified by immunoblotting. DLPC was shown to block ERK1/2 phosphorylation for 30 min after treatment with TNFα (FIG. 1). DLPC was also observed to block a hydrogen peroxide induction of MAPK in SH-SY5Y cells.

Example 2

DLPC Blocks NF-κB Activation

Figure 2:
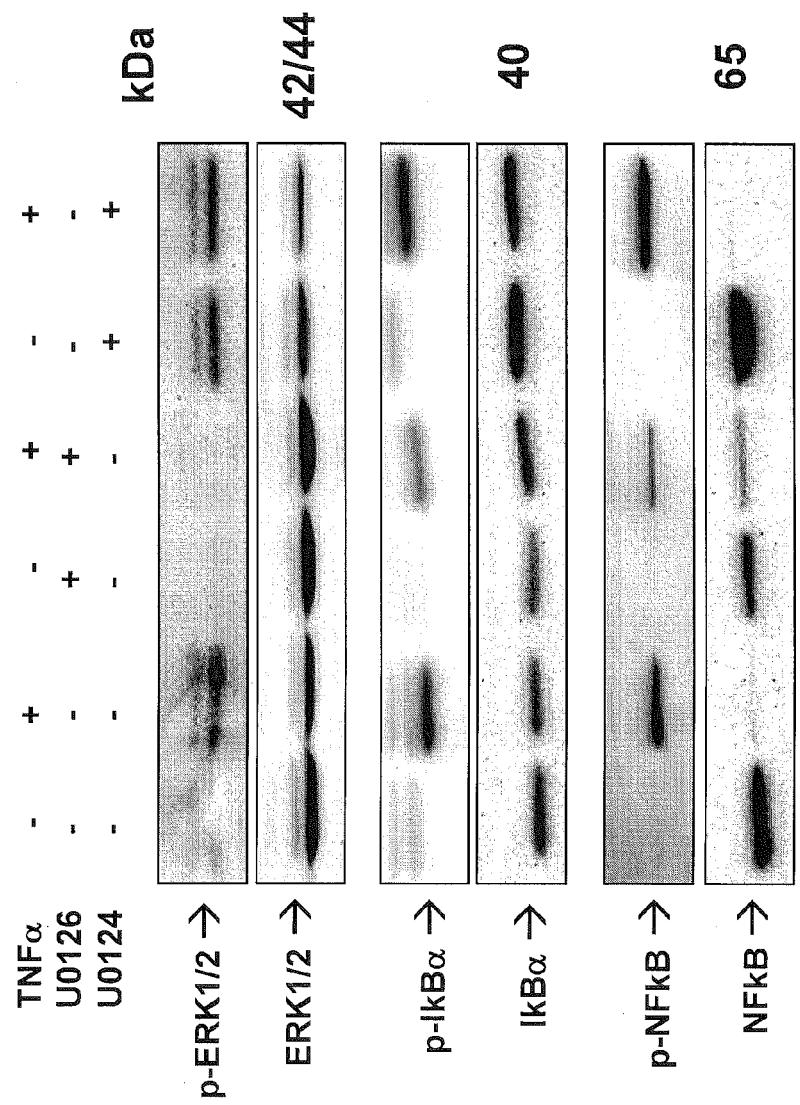
FIG. 2 shows that U0126, a selective MAPK inhibitor, inhibits TNFα-induced ERK and NF-kB phosphorylation. SH-SY5Y cells were pre-incubated with DLPC (12 µM), MAPK-inhibitor U0126 (10 µM) or its inactive analog U0124 (10 µM) for 30 min. and then incubated with TNFα (10 ng/ml) for the indicated times. Phospho and total ERK1/2, IκBα and NF-κB expression were analyzed by Western blotting. Western blots presented are representative of at least 3 independent experiments.
Figure 3:
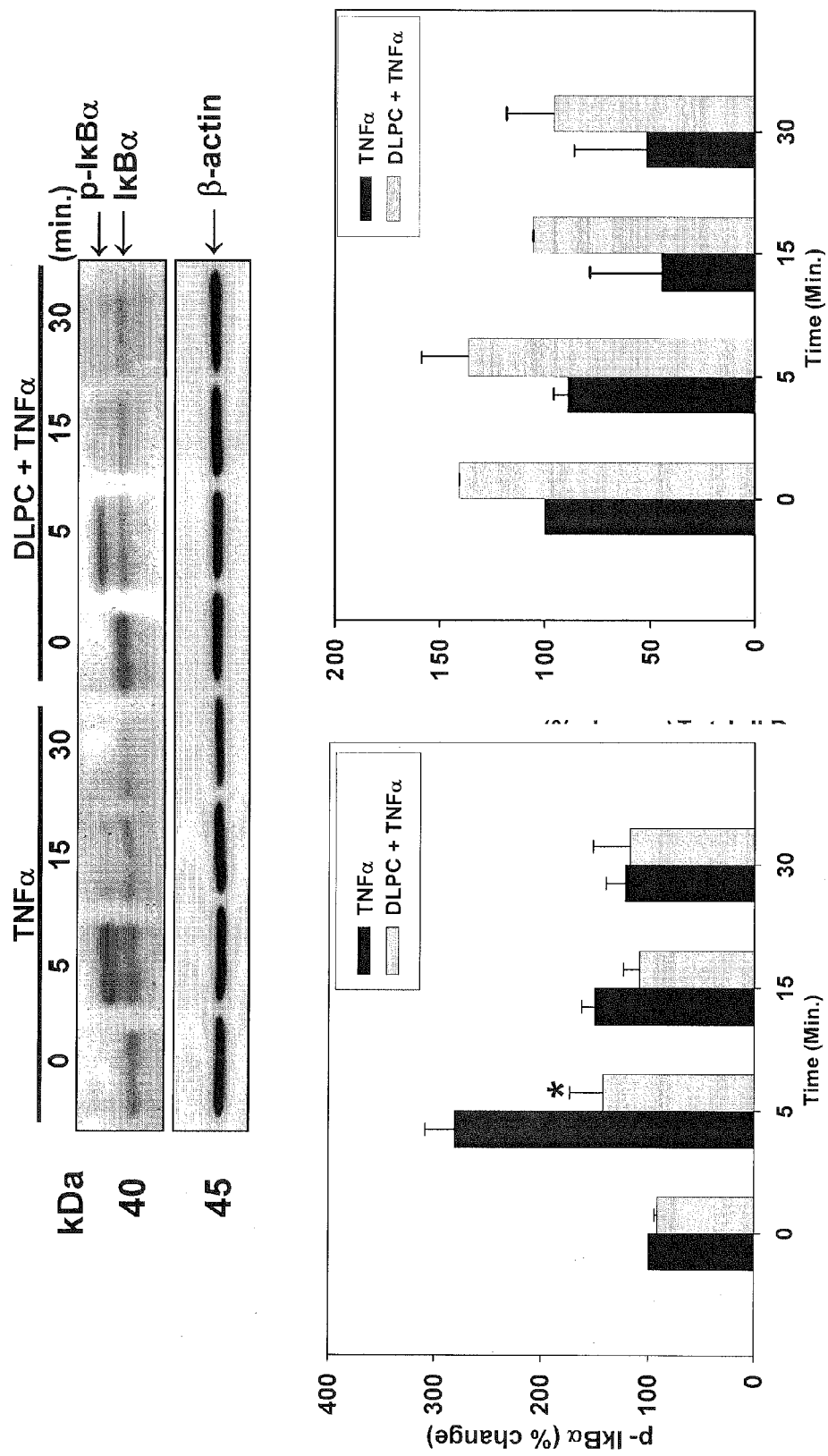
FIG. 3 shows that DLPC inhibits TNFα-induced IκBα phosphorylation and degradation. SH-SY5Y cells were pre-incubated with DLPC (12 µM) for 30 min. and then incubated with TNFα (10 ng/ml) for the indicated times. Phospho and total IκBα expression were analyzed by Western blotting. Histograms representing densitometry analysis of phospho IκBα (P-IκBα) and IκBα and the values are presented relative to total β-actin control and are expressed as mean±SEM of at least 3 independent experiments. *P<0.001 vs TNFα alone.
Figure 4:
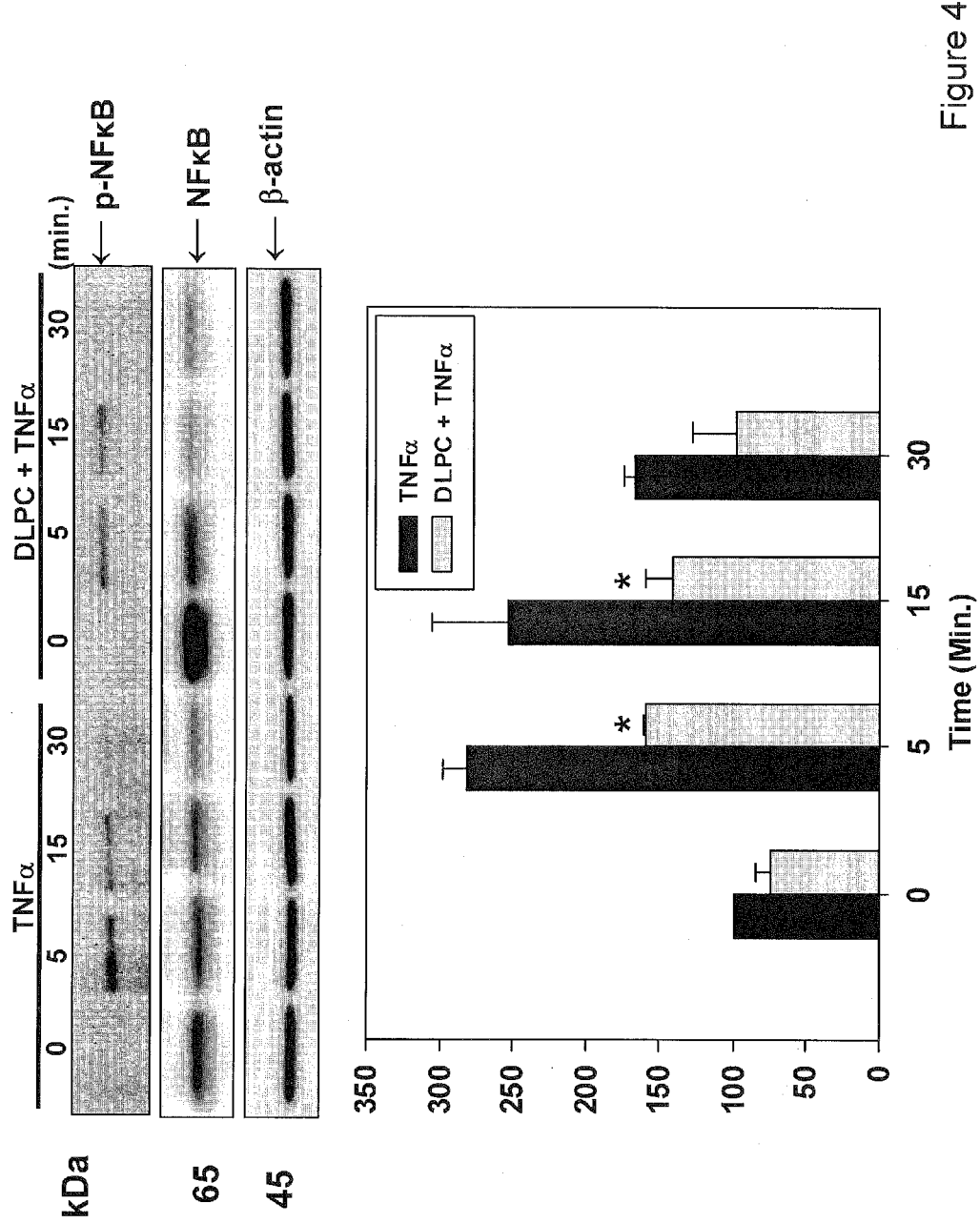
FIG. 4 shows that DLPC inhibits TNFα-induced neuronal NF-κB activation. SH-SY5Y cells were pre-incubated with DLPC (12 µM) for 30 min. and then incubated with TNFα (10 ng/ml) for the indicated times. Phospho and total NF-κB expression were analyzed by Western blotting. Histograms representing densitometry analysis of phospho-NF-κB (P-NF-κB) and NF-κB and the values are presented relative to total β-actin control and are expressed as mean±SEM of at least 3 independent experiments. *P<0.05 vs TNFα alone.

The effect of a selective MAPK inhibitor, U0126, on a TNFα induction of MAPK and nuclear factor kappa B (NF-κB) was evaluated. FIG. 2 shows that pretreatment of SH-SY5Y cells with U0126 (10 μM) for 30 minutes blocked the phosphorylation of ERK1/2 and reduced the phosphorylation of both IκBα and NF-κB by ~50%. Treatment with the inactive analog, UO124, had no effect on ERK1/2 and NF-κB phosphorylation status. DLPC treatment of SH-SY5Y cells blocked TNFα-induced IkBα phosphorylation (FIG. 3, left panel) and prevented IkBα degradation (FIG. 3, right panel). DLPC also inhibited TNFα-induced NF-κB phosphorylation. TNFα induced a 3-fold increase in NF-κB phosphorylation in SH-SY5Y cells at 5 min after treatment (FIG. 4). DLPC blocked the increase in neuronal NF-κB phosphorylation by ~50% over 5-30 min post treatment with TNFα.

Example 3

DLPC Blocks Tau Phosphorylation

Figure 5:
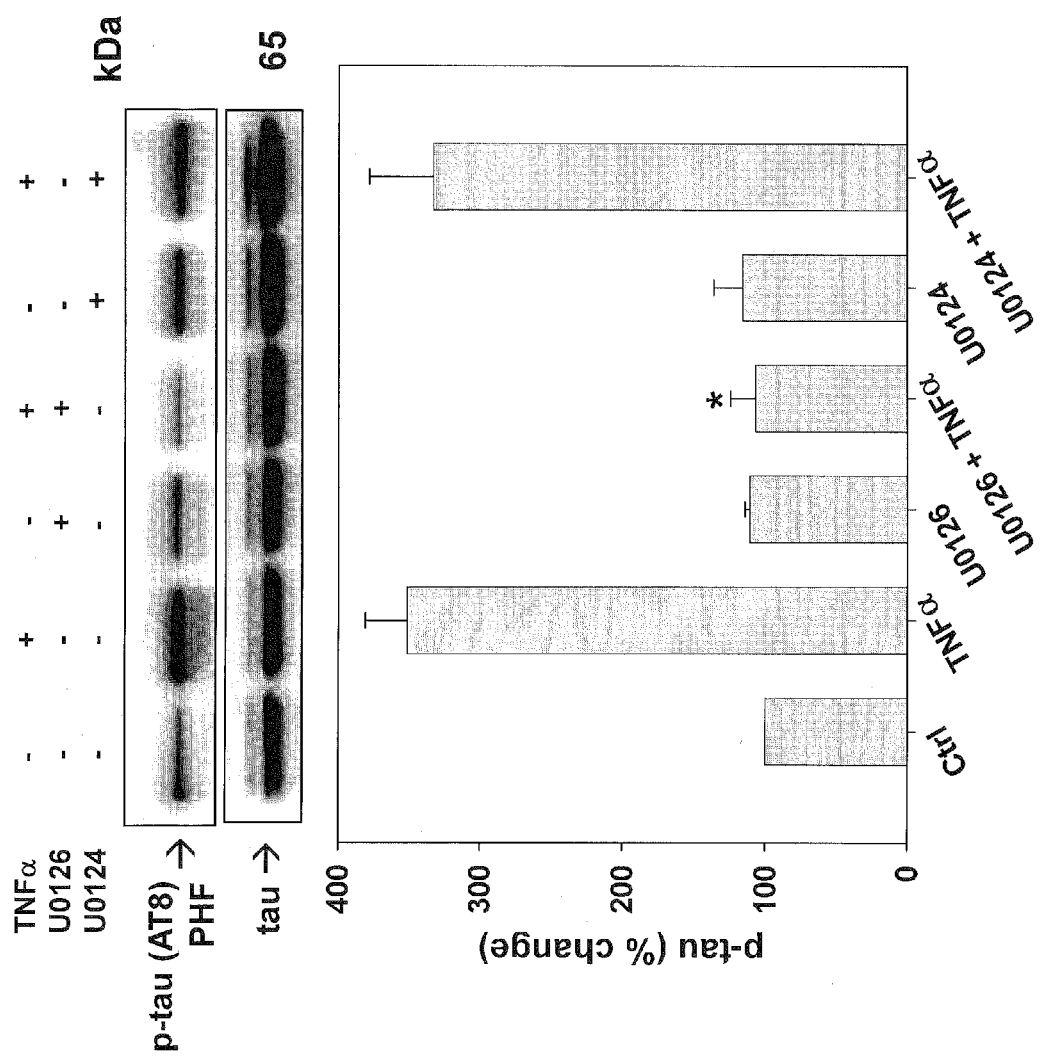
FIG. 5 shows that UO126 blocks TNFα-induced tau phosphorylation. SH-SY5Y cells were pre-incubated with U0126 (10 µM) or U0124 for 30 min and then incubated with TNFα (10 ng/ml) for 5 minutes. Phospho and total tau expression were analyzed by Western blotting. Histograms representing densitometry analysis of phospho and total tau are presented relative to control values and are expressed as mean±SEM of at least 3 independent experiments. *P<0.001 vs TNFα alone.
Figure 6:
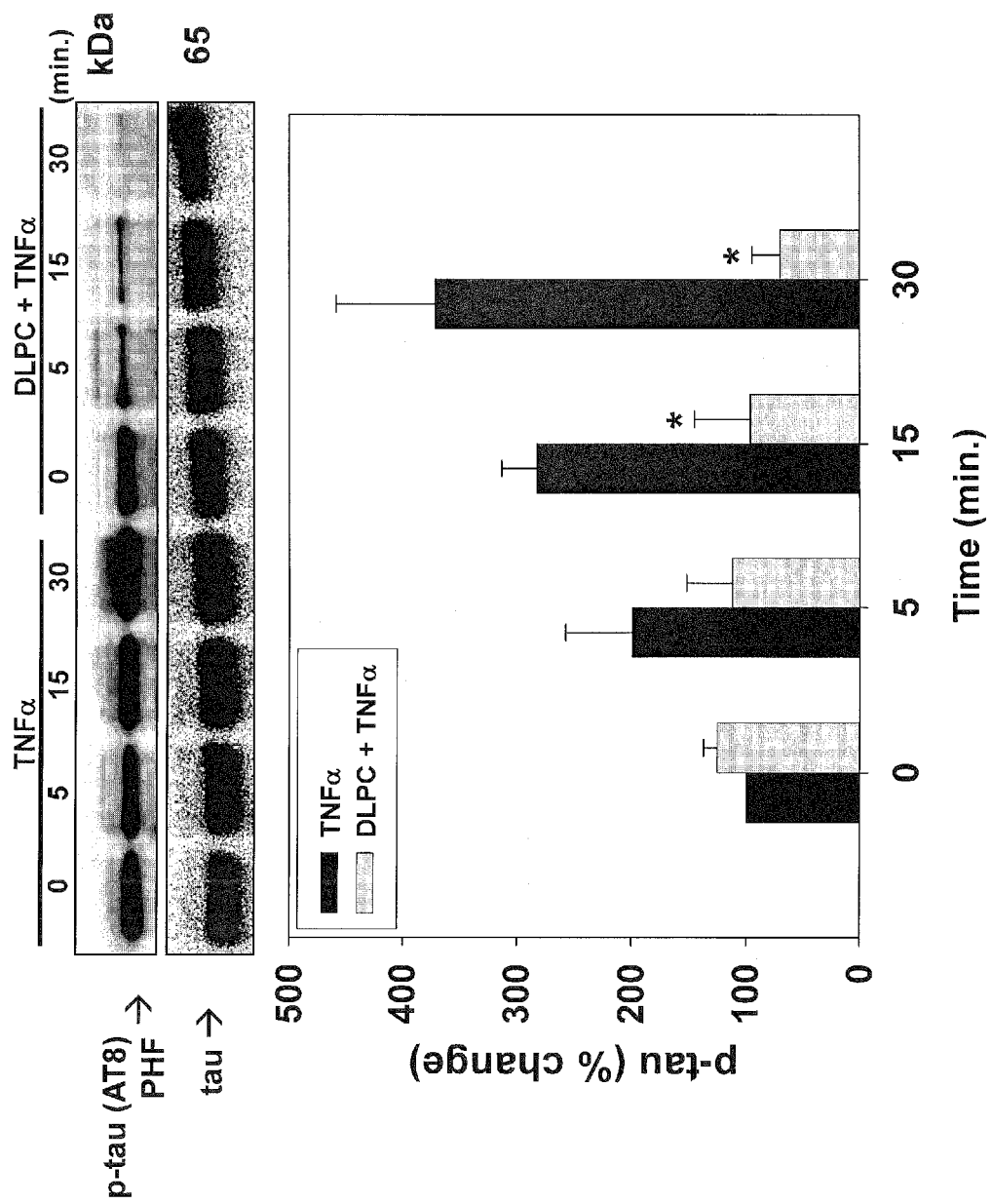
FIG. 6 shows that TNFα-induced tau phosphorylation is blocked by DLPC. SH-SY5Y cells were pre-incubated incubated with DLPC (12 µM) for 30 min and incubated with α (10 ng/ml) for indicated times. Phospho and total tau expression were analyzed by Western blotting. Histograms representing densitometry analysis of phospho and total tau are presented relative to control values and are expressed as mean±SEM of at least 3 independent experiments. *P<0.001 vs TNFα alone.
Figure 7:
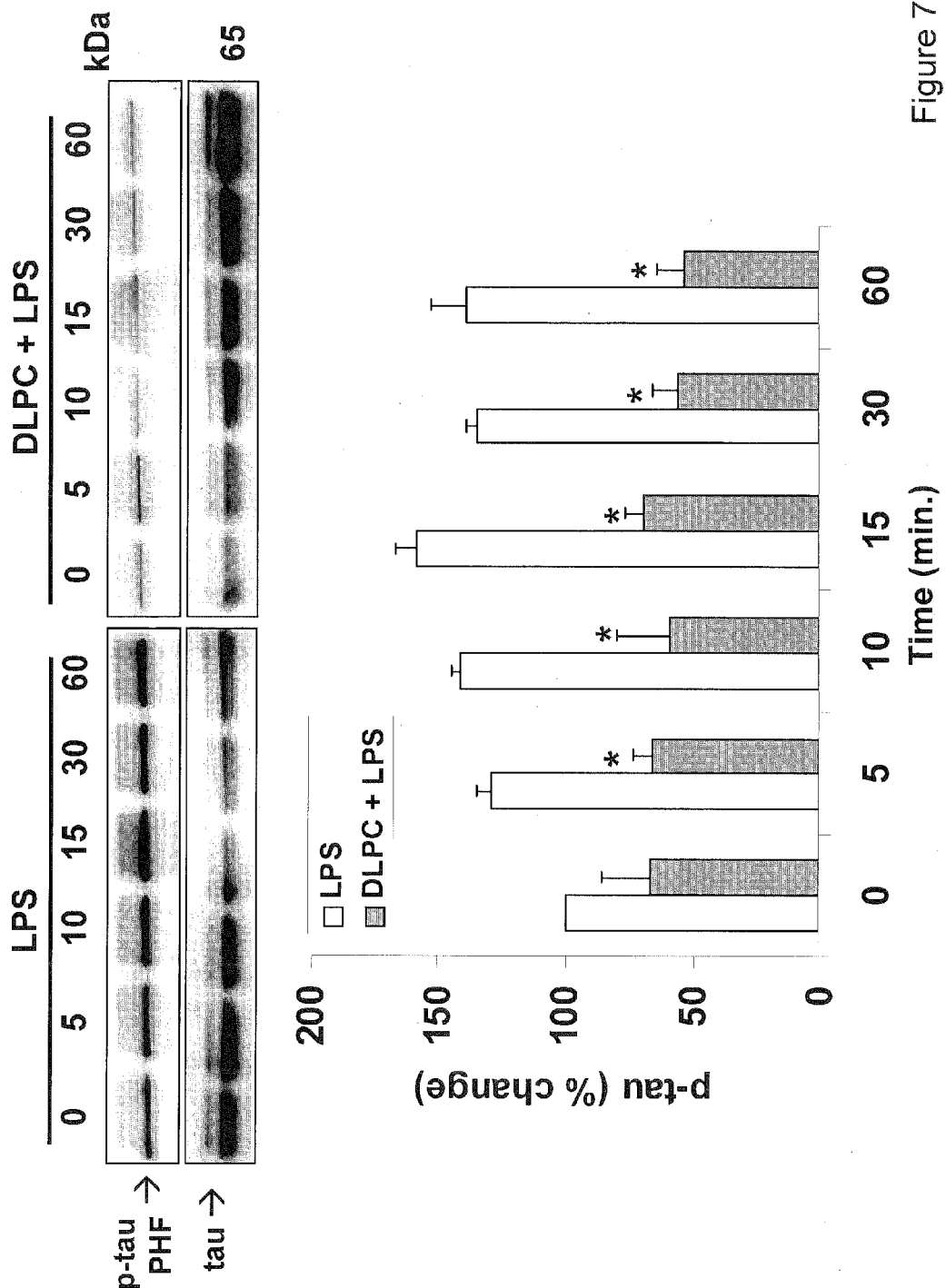
FIG. 7 shows that LPS-induced tau phosphorylation is blocked by DLPC. SH-SY5Y cells were pre-incubated incubated with DLPC (12 µM) for 30 min and incubated with LPS (100 ng/ml) for indicated times. Phospho and total tau expression were analyzed by Western blotting. Histograms representing densitometry analysis of phospho-tau (P-tau) and total tau are presented relative to control values and are expressed as mean±SEM of at least 3 independent experiments. *P<0.001 vs LPS alone.

The effect of pro-inflammatory and oxidative stress agonists on tau phosphorylation were also evaluated in SH-SY5Y cells. Pretreatment of the cells with U0126 completely blocked TNFα-induced phosphorylation of tau (AT8) at 5 min (FIG. 5). TNFα and lipopolysaccharide (LPS) both increased tau phosphorylation and DLPC blocked the effect both agonists and gave rise to tau phoshoylation levels lower than control values by 30 min (FIGS. 6 & 7). Similar results were observed with a hydrogen peroxide induction of tau phosphorylation.

Example 4

DLPC Blocks LPS-Induced Amyloid-β Secretion in SH-SY5Y Cells

Figure 8:
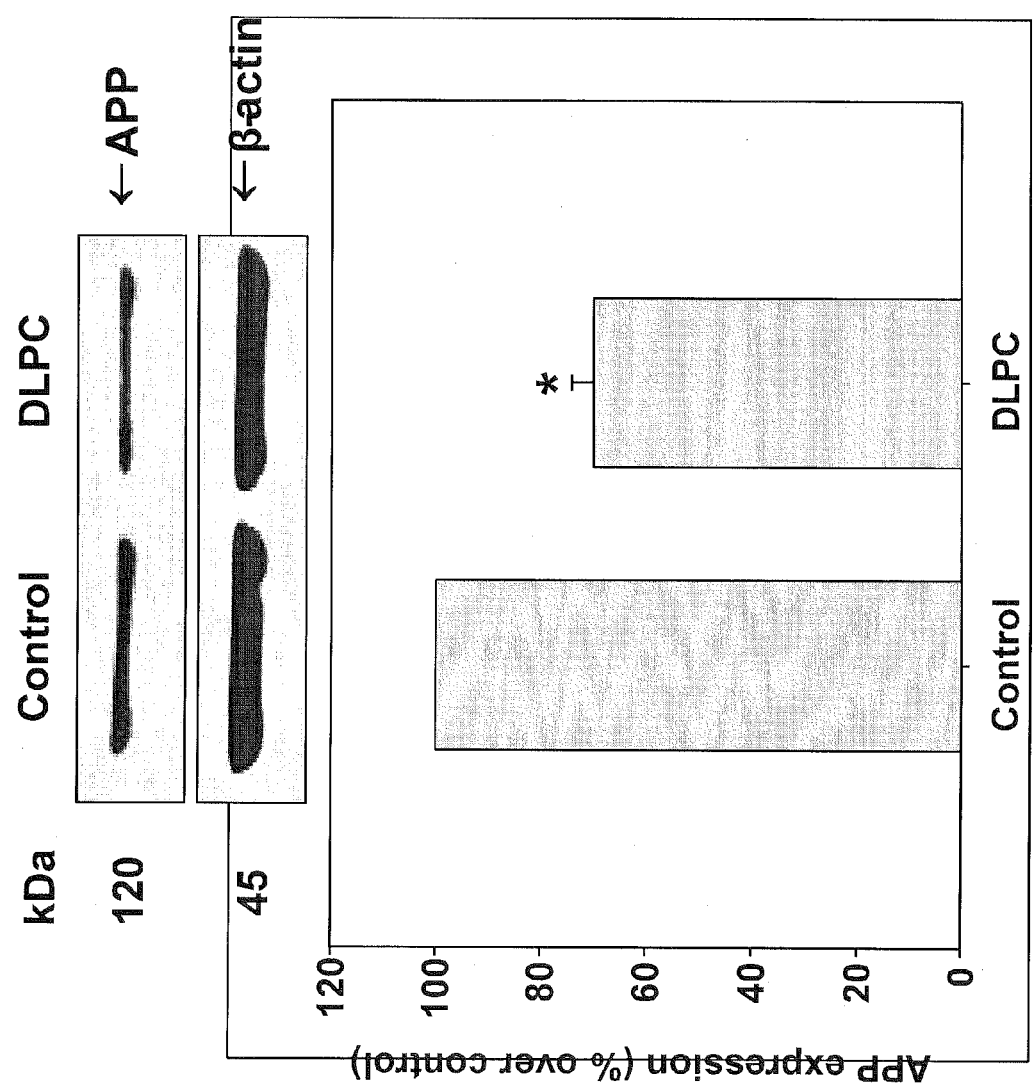
FIG. 8 shows that DLPC blocks basal amyloid precursor protein (APP) expression. SH-SY5Y cells were incubated with DLPC (12 µM) for 24 h and APP expression was analyzed in total cell lysates by Western blotting. Histograms representing densitometry analysis of APP and the values are presented relative to total β-actin control and are expressed as mean±SEM of at least 3 independent experiments. *P<0.05 vs control.
Figure 9:
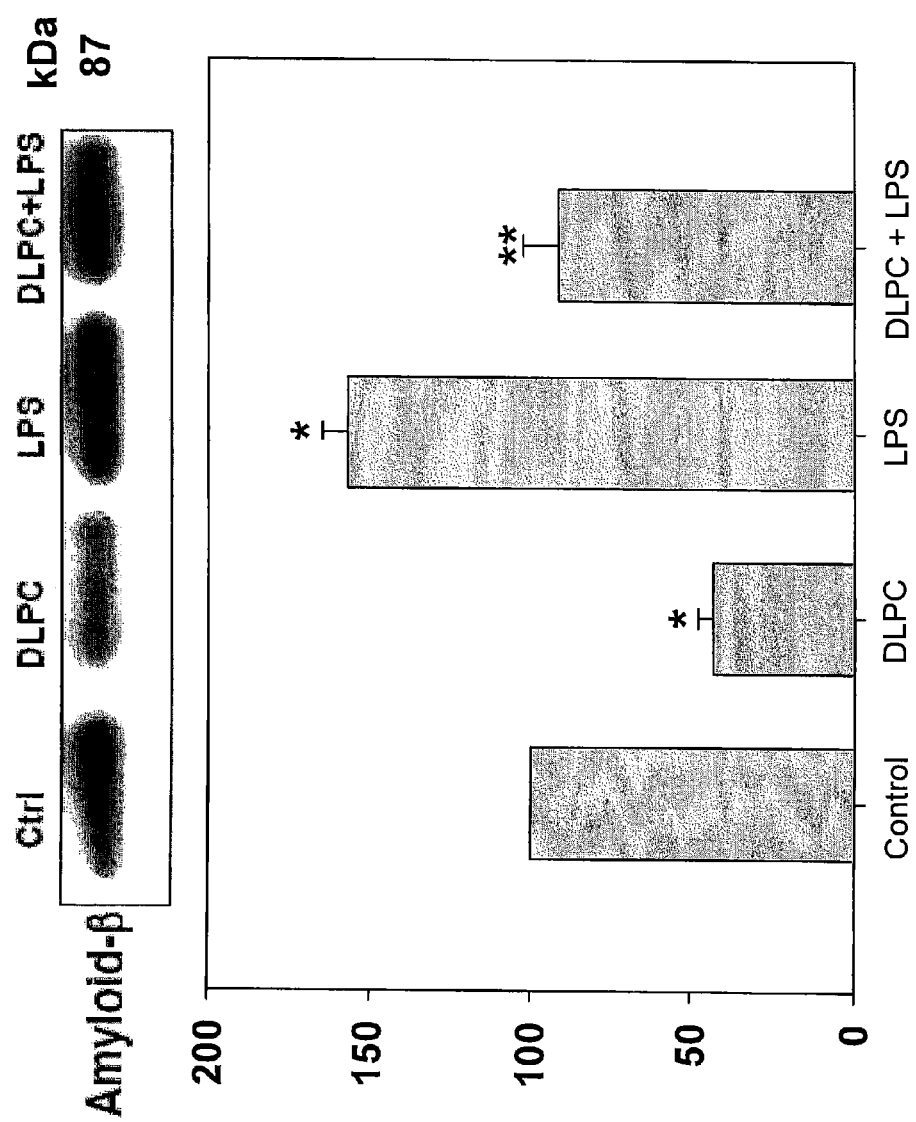
FIG. 9 shows that LPS-induced amyloid-β secretion is blocked by DLPC. SH-SY5Y cells were pretreated with DLPC (12 µM) for 30 minutes and then incubated with LPS (100 ng/mL) for 24 h. Conditioned media from each experiment were collected and subjected to Western blot analysis for amyloid-β. Loading volumes were adjusted relative to total cell protein. Histograms representing densitometry analysis of amyloid-β and are expressed as mean±SEM of at least 3 independent experiments. *P<0.001 vs control and **P<0.001 vs LPS alone.

FIG. 8 shows that DLPC decreased the basal expression of amyloid precursor protein (APP) by ~25% in unstimulated neuroblastoma cells. Treatment of SH-SY5Y cells with LPS for 24 h significantly increased amyloid-beta (Aβ) expression and secretion (FIG. 9). DLPC decreased the basal secretion of Aβ from SH-SY5Y cells by 65% and completely blocked the LPS-induced increase in Aβ secretion (FIG. 9).

Inflammation is casual to neurodegeneration in AD and neuronal response to inflammatory stimuli is governed by both MAPK and NF-κB pathways. Studies have shown that MAPK plays a role in the activation of NF-κB and induction of TNFα production (37-39). DLPC acts through MAPK to prevent activation of NF-κB. DLPC is able to completely block a peroxide and TNFα activation of MAPK in SH-SY5Y cells by preventing phosphorylation of ERK 1/2 (FIG. 1). This result is similar to that observed with other ERK phosphorylation inhibitors. U0126 is MEK 1/2 specific inhibitor that blocks ERK phosphorylation and inhibits AP-1, a potent transcriptional regulator of immune response genes (40). Inhibition of MAPK activation with U0126 has been previously shown to block Aβ induction of NF-κB, COX-2 expression and PGE(2) production (37).

Linoleic PL act to block NF-κB activation in SH-SY5Y cells by preventing the phosphorylation of IkBα and NF-κB (FIGS. 3 & 4). DLPC blocks a TNFα-induced phosphorylation of IkBα and thereby prevents the ubiquitylation-induced reduction in cellular IkBα levels (FIG. 3, right panel). A reduction in IkBα phosphorylation would be expected to prevent NF-κB phosphorylation and FIG. 4 confirms this view. Other experiments by the inventors of the instant application have indicated that DLPC can block an LPS and TNFα induction of NF-κB in HepG2 and CaCO-2 cell lines (Pandey et al. unpublished observations). Studies in other laboratories have shown that DLPC is anti-apoptotic (41) and decreases induction of TNFα secretion and NF-κB activation in Kupffer cells of ethanol-fed rats (14,15). DLPC therefore has significant NF-κB inhibitory activity in different tissues.

One of the earliest AD mechanistic hypotheses involves the inflammatory-induced accumulation of hyperphosphorylated tau proteins in the neuron (42,43). Tau hyperphosphorylation in neuronal cells is initiated by MAPK activation (44). The protein is phosphorylated by both the stress kinase p38 and glycogen synthase kinase 3 (GSK3) (45) and GSK3 is activated by Aβ and p38 by oxidative stress. Oxidative stress, LPS and TNFα all increase tau phosphorylation in SH-SY5Y cells and DLPC prevents the hyperphosphoylation (FIGS. 6 & 7). Tau fibrilliary tangles are believed to promote microtubule disintegration and destroy the neuron's transport system and therefore DLPC is expected to prevent neuronal malfunction and cell death.

AD is also thought to be a protein misfolding disease and results in the accumulation of abnormally folded amyloid protein fragments in the brains of AD patients (46-48). Aβ[1-42] is the more pathogenic fragment that is associated with disease states. To determine if linoleic PL impact the amyloid metabolism in SH-SY5Y cells, basal amyloid precursor protein (APP) and Aβ levels were probed in cells treated with DPLC. PL treated cells showed a significant reduction in basal APP levels (FIG. 8) and a 65% reduction in basal Aβ secretion (FIG. 9). LPS caused a >1.5-fold stimulation in Aβ secretion, which was blocked by DLPC (FIG. 9). Aβ secretion has been linked to an activation of MAPK and NF-κB (49-51) and therefore it is expected that an inhibition of these pathways reduces the production secretion of Aβ. Aβ production appears to be reduced by α-secretase activity and insulin-degrading enzyme, which catabolizes Aβ. Therapeutic strategies that regulate secretase activity and reduce Aβ secretion have shown some promise (52,53).

PL enriched in unsaturated fatty acids are crucial to the normal neurological function of the brain. Neurodegeneration has been shown to be associated with abnormal phospholipid metabolism in the brain (54-56). Brain tissue from AD patients has been shown to have alternations in brain membrane composition and metabolism (57-60). Most notably, AD brains are deficient in unsaturated phospholipids and enriched with saturated (57). Erythrocyte membrane phospholipid composition has been shown to correlate to brain phospholipid composition (61) and may be a useful marker for neurological disease (62,63). Since erythrocyte phospholipid composition is impacted by dietary habits, the therapeutic administration of linoleic PL, such as DLPC, is expected to increase the concentration of these lipids in both the plasma and brain and promote neuronal anti-inflammatory events, by directly inhibiting NF-κB.

Example 5

DLPC Modulation of Inflammatory Pathways

Figure 10:
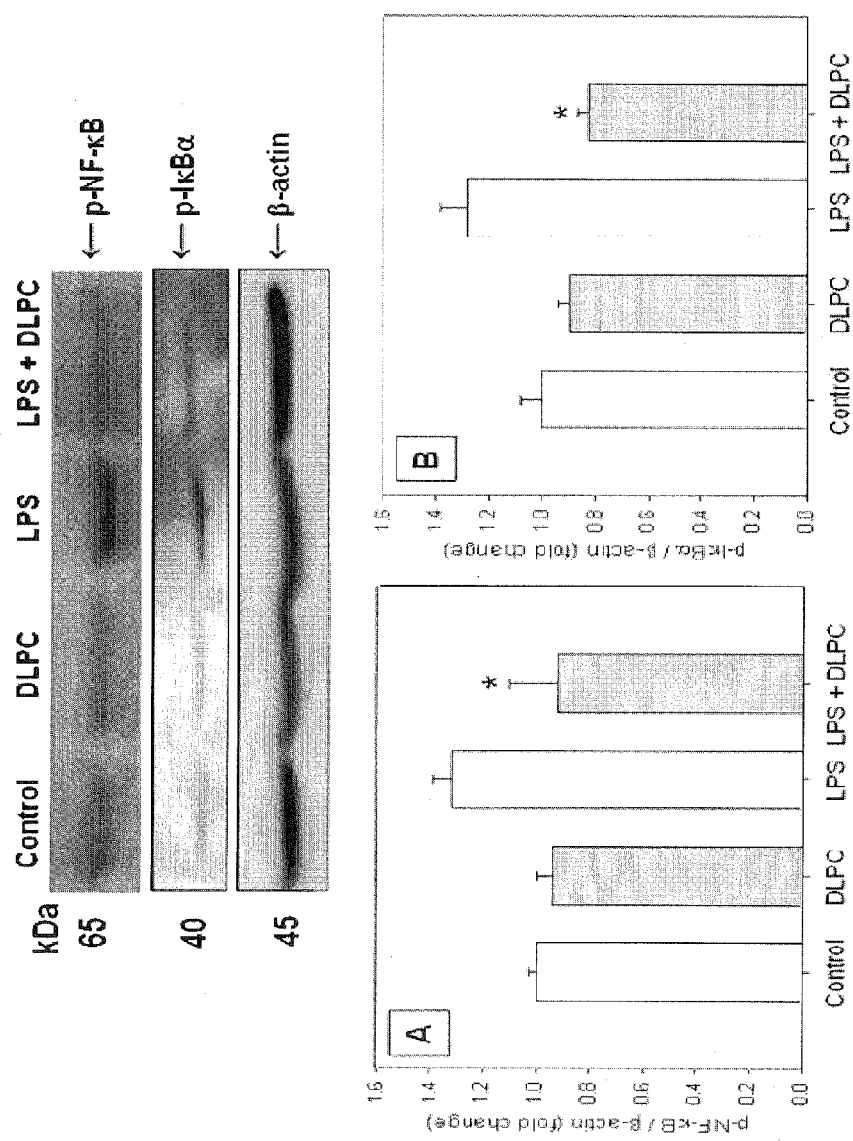
FIG. 10 shows results that DLPC inhibits LPS-induced IκBα and NF-κB phosphorylation after 24 h. HepG2 cells were pre-incubated with DLPC (12 µM) for 30 min. and then incubated with LPS (5 µg/ml) for 24 h in DMEM serum-depleted media. Phospho-IκBα and phospho-NF-kB (p-IκBα and p-NF-κB) expression were analyzed by Western blot. Histograms represent densitometry analysis of p-IκBα (A) and p-NF-κB (B) and values are shown relative to β-actin and are expressed as mean±SEM of 3 replicate experiments. *P<0.05 vs LPS alone.
Figure 11:
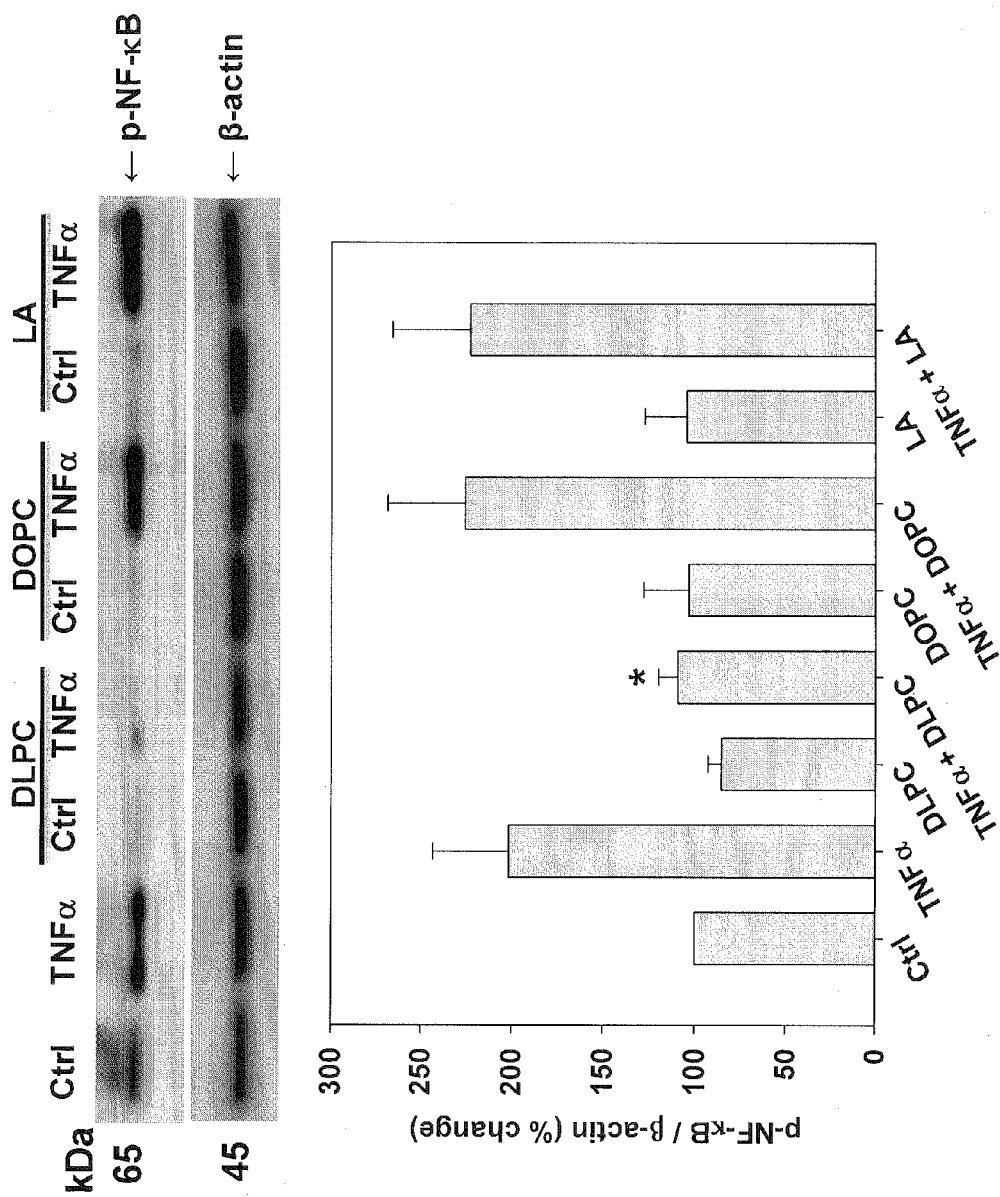
FIG. 11 shows results that linoleic acid phospholipids block activation of NF-κB. HepG2 cells were incubated with DLPC (12 µmol/L), dioleoyl phosphatidylcholine (DOPC) (12 µmol/L) or linoleic acid (LA) (25 µmol/L) for 30 min, TNFα (10 ng/ml) for 5 min and then cell lysates were analyzed for p-NF-κB by Western blot. Values are shown relative to β-actin and are expressed as mean±SEM of 3 replicate experiments. *P<0.05 vs TNFα alone.

Linoleic acid phospholipids (PL) affect inflammatory pathways in cells of the body, much like glucocorticoids, by neutralizing NF-κB activation. This is further exemplified by studies in human liver (HepG2) cells. PL impact NF-κB phosphorylation by 5 min and maintain a reduced activation state in human liver cells for 24 h (FIG. 10A). A reduced NF-κB phosphorylation is associated with a parallel reduction in the phosphorylation of IkBα (FIG. 10B). Inhibition of IkBα and NF-κB phosphorylation is dependent on the linoleic acid content of PL. Phospholipids containing oleic acid (DOPC) and the pure fatty acid, linoleic acid, have no impact on the activation of NF-κB (FIG. 11).

Figure 12:
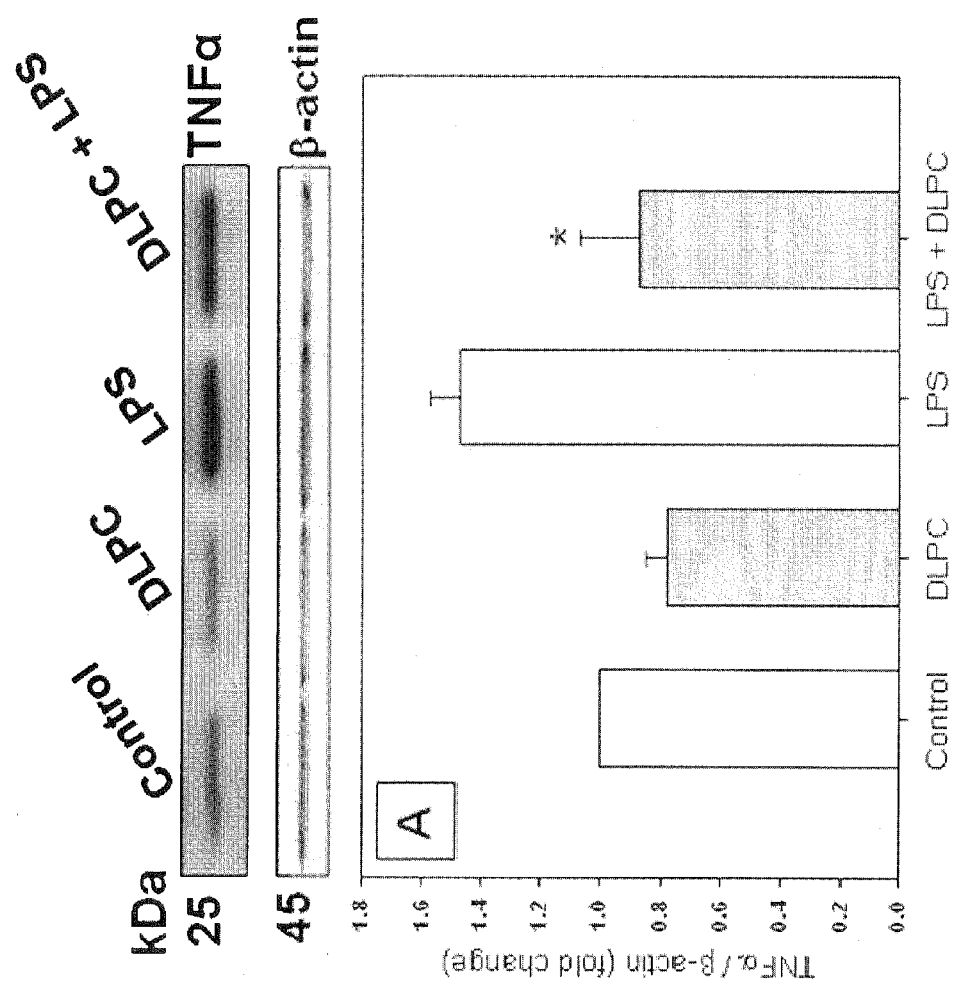
FIG. 12 shows results that DLPC blocks LPS-induced TNFα expression. HepG2 cells were pre-incubated with DLPC (12 µmol/L) for 30 min and then incubated with LPS (5 µg/ml) for 24 h in DMEM serum-depleted media. Cell lysates were analyzed for TNFα expression by Western blot. Values are presented relative to β-actin and are expressed as mean±SEM for 3 replicate experiments. *P<0.05 vs LPS alone.
Figure 13:
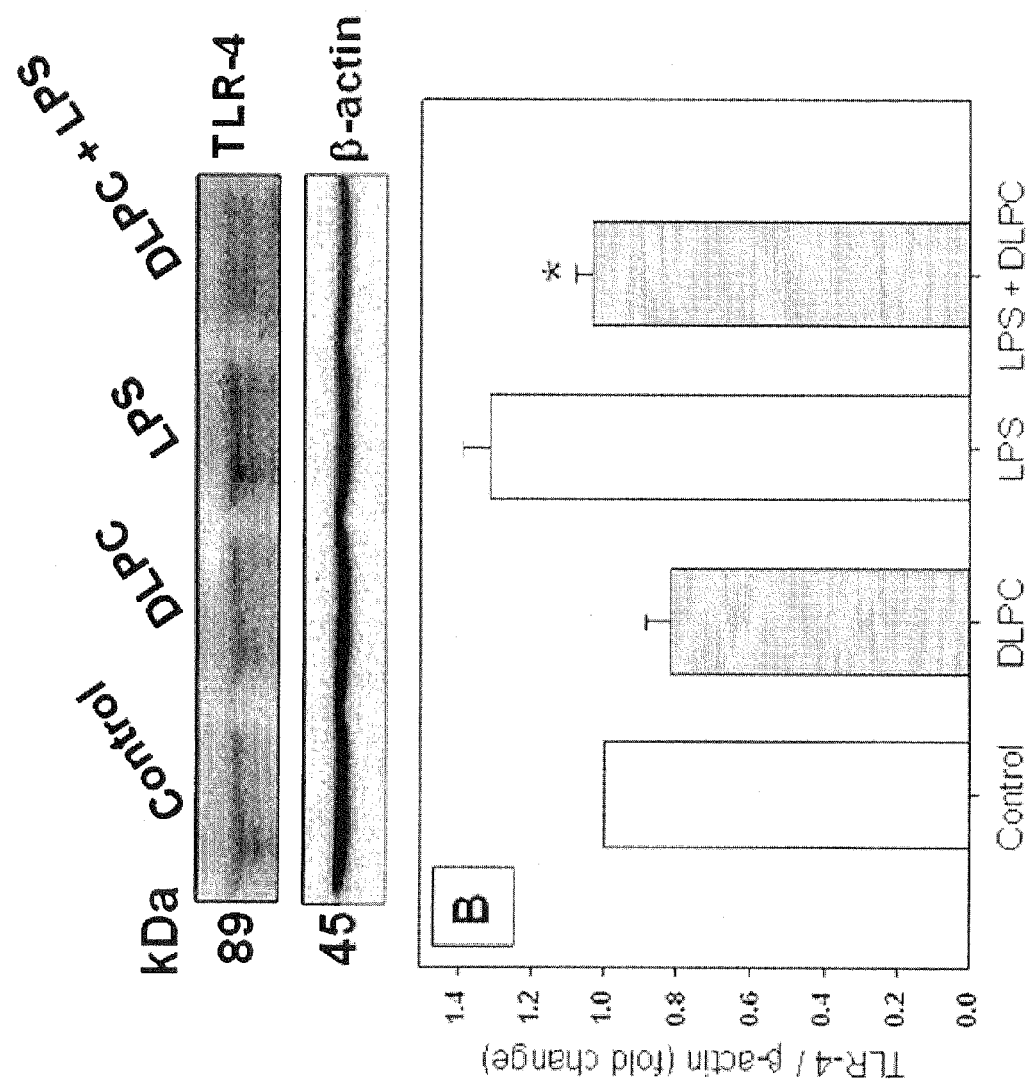
FIG. 13 shows results that DLPC blocks LPS-induced TLR-4 expression. HepG2 cells were pre-incubated with DLPC (12 µmol/L) for 30 min. and then incubated with LPS (5 µg/ml) for 24 h in DMEM serum-depleted media. Cell lysates were analyzed for TLR-4 expression by Western blot. Values are presented relative to β-actin and are expressed as mean±SEM for 3 replicate experiments. *P<0.05 vs LPS alone.

A prolonged inhibition in NF-κB activation would be expected to impact the production of pro-inflammatory cytokines, such as TNFα. DLPC inhibits activation of NF-κB in HepG2 cells for up to 24 h and consequently inhibits an LPS-induced increase in TNFα expression (FIG. 12). Decreased TNFα expression may also be a consequence of a reduced TLR-4 expression. DLPC blocks an LPS-induced increase in TLR-4 expression (FIG. 13). The family of Toll-like receptors is known to initiate an innate immune response to pathogens, such as LPS, and TLR-4 is known to play a central role in the activation of NF-κB.

Although this invention is described in detail with reference to preferred embodiments thereof, these embodiments are offered to illustrate but not to limit the invention. It is possible to make other embodiments that employ the principles of the invention and that fall within its scope as defined by the claims appended hereto.

All citations are hereby incorporated by reference.

REFERENCES

1. Selkoe, D. J. (2001) Alzheimer's disease: genes, proteins, and therapy, *Physiol Rev.* 81, 741-766.
2. McGeer, P. L., Schulzer, M., and McGeer, E. G. (1996) Arthritis and anti-inflammatory agents as possible protective factors for Alzheimer's disease: a review of 17 epidemiologic studies, *Neurology* 47, 425-432.
3. Kalaria, R. N. (1999) Microglia and Alzheimer's disease, *Curr. Opin. Hematol.* 6, 15-24.
4. Akiyama, H., Barger, S., Barnum, S., Bradt, B., Bauer, J., Cole, G. M., Cooper, N. R., Eikelenboom, P., Emmerling, M., Fiebich, B. L., Finch, C. E., Frautschy, S., Griffin, W. S., Hampel, H., Hull, M., Landreth, G., Lue, L., Mrak, R., Mackenzie, I. R., McGeer, P. L., O'Banion, M. K., Pachter, J., Pasinetti, G., Plata-Salaman, C., Rogers, J., Rydel, R., Shen, Y., Streit, W., Strohmeyer, R., Tooyoma, I., Van Muiswinkel, F. L., Veerhuis, R., Walker, D., Webster, S., Wegrzyniak, B., Wenk, G., and Wyss-Coray, T. (2000) Inflammation and Alzheimer's disease, *Neurobiol. Aging* 21, 383-421.
5. Paris, D., Patel, N., Quadros, A., Linan, M., Bakshi, P., it-Ghezala, G., and Mullan, M. (2007) Inhibition of Abeta production by NF-kappaB inhibitors, *Neurosci. Lett.* 415, 11-16.
6. Bales, K. R., Du, Y., Dodel, R. C., Yan, G. M., Hamilton-Byrd, E., and Paul, S. M. (1998) The NF-kappaB/Rel family of proteins mediates Abeta-induced neurotoxicity and glial activation, *Brain Res. Mol. Brain. Res.* 57, 63-72.
7. Sung, S., Yang, H., Uryu, K., Lee, E. B., Zhao, L., Shineman, D., Trojanowski, J. Q., Lee, V. M., and Pratico, D. (2004) Modulation of nuclear factor-kappa B activity by indomethacin influences A beta levels but not A beta precursor protein metabolism in a model of Alzheimer's disease, *Am. J. Pathol.* 165, 2197-2206.
8. Pandey, N. R., Renwick, J., Misquith, A., Sokoll, K., and Sparks, D. L. (2008) Linoleic Acid-Enriched Phospholipids Act through Peroxisome Proliferator-Activated Receptors alpha To Stimulate Hepatic Apolipoprotein A-I Secretion, *Biochemistry* 47, 1579-1587.
9. Pandey, N. R. and Sparks, D. L. (2008) Phospholipids as cardiovascular therapeutics, *Curr. Opin. Investig. Drugs.* 9, 281-285.
10. Barter, P., Kastelein, J., Nunn, A., and Hobbs, R. (2003) High density lipoproteins (HDLs) and atherosclerosis; the unanswered questions, *Atherosclerosis* 168, 195-211.
11. Barter, P. J., Puranik, R., and Rye, K. A. (2007) New insights into the role of HDL as an anti-inflammatory agent in the prevention of cardiovascular disease, *Curr. Cardiol. Rep.* 9, 493-498.
12. Thoenes, M., Oguchi, A., Nagamia, S., Vaccari, C. S., Hammoud, R., Umpierrez, G. E., and Khan, B. V. (2007) The effects of extended-release niacin on carotid intimal media thickness, endothelial function and inflammatory markers in patients with the metabolic syndrome, *Int. J. Clin. Pract.* 61, 1942-1948.
13. Kuvin, J. T., Dave, D. M., Sliney, K. A., Mooney, P., Patel, A. R., Kimmelstiel, C. D., and Karas, R. H. (2006) Effects of extended-release niacin on lipoprotein particle size, distribution, and inflammatory markers in patients with coronary artery disease, *Am. J. Cardiol.* 98, 743-745.
14. Cao, Q., Mak, K. M., and Lieber, C. S. (2002) Dilinoleoylphosphatidylcholine decreases LPS-induced TNF-alpha generation in Kupffer cells of ethanol-fed rats: respective roles of MAPKs and NF-kappaB, *Biochem. Biophys. Res. Commun.* 294, 849-853.
15. Cao, Q., Mak, K. M., and Lieber, C. S. (2002) Dilinoleoylphosphatidylcholine decreases acetaldehyde-induced TNF-alpha generation in Kupffer cells of ethanol-fed rats, *Biochem. Biophys. Res. Commun.* 299, 459-464.
16. Oneta, C. M., Mak, K. M., and Lieber, C. S. (1999) Dilinoleoylphosphatidylcholine selectively modulates lipopolysaccharide-induced Kupffer cell activation, *J. Lab Clin. Med.* 134, 466-470.
17. Treede, I., Braun, A., Sparla, R., Kuhnel, M., Giese, T., Turner, J. R., Anes, E., Kulaksiz, H., Fullekrug, J., Stremmel, W., Griffiths, G., and Ehehalt, R. (2007) Anti-inflammatory effects of phosphatidylcholine, *J. Biol. Chem.* 282, 27155-27164.
18. Little, A., Levy, R., Chuaqui-Kidd, P., and Hand, D. (1985) A double-blind, placebo controlled trial of high-dose lecithin in Alzheimer's disease, *J. Neurol. Neurosurg. Psychiatry* 48, 736-742.
19. Higgins, J. P. and Flicker, L. (2003) Lecithin for dementia and cognitive impairment, *Cochrane. Database. Syst. Rev.* CD001015.
20. Funfgeld, E. W., Baggen, M., Nedwidek, P., Richstein, B., and Mistlberger, G. (1989) Double-blind study with phosphatidylserine (PS) in parkinsonian patients with senile dementia of Alzheimer's type (SDAT), *Prog. Clin. Biol. Res.* 317, 1235-1246.
21. Amaducci, L., Crook, T. H., Lippi, A., Bracco, L., Baldereschi, M., Latorraca, S., Piersanti, P., Tesco, G., and Sorbi, S. (1991) Use of phosphatidylserine in Alzheimer's disease, *Ann. N.Y. Acad. Sci.* 640, 245-249.
22. Crook, T., Petrie, W., Wells, C., and Massari, D. C. (1992) Effects of phosphatidylserine in Alzheimer's disease, *Psychopharmacol. Bull.* 28, 61-66.
23. Engel, R. R., Satzger, W., Gunther, W., Kathmann, N., Bove, D., Gerke, S., Munch, U., and Hippius, H. (1992) Double-blind cross-over study of phosphatidylserine vs. placebo in patients with early dementia of the Alzheimer type, *Eur. Neuropsychopharmacol.* 2, 149-155.
24. Schreiber, S., Kampf-Sherf, O., Gorfine, M., Kelly, D., Oppenheim, Y., and Lerer, B. (2000) An open trial of plant-source derived phosphatydilserine for treatment of age-related cognitive decline, *Isr. J. Psychiatry Relat Sci.* 37, 302-307.
25. Hopewell, S., Pandey, N. R., Misquith, A., Twomey, E., and Sparks, D. L. (2008) Phosphatidylinositol acts through mitogen-activated protein kinase to stimulate hepatic apolipoprotein A-I secretion, *Metabolism* 57, 1677-1684.
26. Wilson, T. A., Meservey, C. M., and Nicolosi, R. J. (1998) Soy lecithin reduces plasma lipoprotein cholesterol and early atherogenesis in hypercholesterolemic monkeys and hamsters: beyond linoleate, *Atherosclerosis* 140, 147-153.
27. Lieber, C. S. (2000) Alcoholic liver disease: new insights in pathogenesis lead to new treatments, *J. Hepatol.* 32, 113-128.
28. Lieber, C. S. (2005) Pathogenesis and treatment of alcoholic liver disease: progress over the last 50 years, *Rocz. Akad. Med. Bialymst.* 50, 7-20.
29. Stremmel, W., Merle, U., Zahn, A., Autschbach, F., Hinz, U., and Ehehalt, R. (2005) Retarded release phosphatidylcholine benefits patients with chronic active ulcerative colitis, *Gut* 54, 966-971.
30. Chung, S. Y., Moriyama, T., Uezu, E., Uezu, K., Hirata, R., Yohena, N., Masuda, Y., Kokubu, T., and Yamamoto, S. (1995) Administration of phosphatidylcholine increases brain acetylcholine concentration and improves memory in mice with dementia, *J. Nutr.* 125, 1484-1489.
31. Sakai, M., Yamatoya, H., and Kudo, S. (1996) Pharmacological effects of phosphatidylserine enzymatically synthesized from soybean lecithin on brain functions in rodents, *J. Nutr. Sci. Vitaminol. (Tokyo)* 42, 47-54.
32. Suzuki, S., Yamatoya, H., Sakai, M., Kataoka, A., Furushiro, M., and Kudo, S. (2001) Oral administration of soybean lecithin transphosphatidylated phosphatidylserine improves memory impairment in aged rats, *J. Nutr.* 131, 2951-2956.
33. Burgess, J. W., Neville, T. A., Rouillard, P., Harder, Z., Beanlands, D. S., and Sparks, D. L. (2005) Phosphatidylinositol increases HDL-C levels in humans, J. Lipid Res. 46, 350-355.
34. Merched, A., Xia, Y., Visvikis, S., Serot, J. M., and Siest, G. (2000) Decreased high-density lipoprotein cholesterol and serum apolipoprotein A1 concentrations are highly correlated with the severity of Alzheimer's disease, *Neurobiol. Aging* 21, 27-30.

35. Fan, P., Liu, Y., Zhang, Z., Liu, B., Ge, W., Ye, S., Cheng, Y., and Chen, J. (2001) [Serum apolipoprotein A I, B100 and E levels and apolipoprotein E polymorphism in patients with Alzheimer's disease and multiple infarction dementia in Chinese population], Hua Xi. Yi. Ke. Da. Xue. Xue. Bao. 32, 389-391.
36. Morris, M. C., Evans, D. A., Bienias, J. L., Scherr, P. A., Tangney, C. C., Hebert, L. E., Bennett, D. A., Wilson, R. S., and Aggarwal, N. (2004) Dietary niacin and the risk of incident Alzheimer's disease and of cognitive decline, J. Neurol. Neurosurg. Psychiatry 75, 1093-1099.
37. Jang, J. H. and Surh, Y. J. (2005) Beta-amyloid-induced apoptosis is associated with cyclooxygenase-2 up-regulation via the mitogen-activated protein kinase-NF-kappaB signaling pathway, Free Radic. Biol. Med. 38, 1604-1613.
38. Lecureur, V., Ferree, E. L., N'diaye, M., Vee, M. L., Gardyn, C., Gilot, D., and Fardel, O. (2005) ERK-dependent induction of TNFalpha expression by the environmental contaminant benzo(a)pyrene in primary human macrophages, FEBS Lett. 579, 1904-1910.
39. Wu, D. and Cederbaum, A. (2008) Cytochrome P4502E1 sensitizes to tumor necrosis factor alpha-induced liver injury through activation of mitogen-activated protein kinases in mice, Hepatology 47, 1005-1017.
40. Duncia, J. V., Santella, J. B., III, Higley, C. A., Pitts, W. J., Wityak, J., Frietze, W. E., Rankin, F. W., Sun, J. H., Earl, R. A., Tabaka, A. C., Teleha, C. A., Blom, K. F., Favata, M. F., Manos, E. J., Daulerio, A. J., Stradley, D. A., Horiuchi, K., Copeland, R. A., Scherle, P. A., Trzaskos, J. M., Magolda, R. L., Trainor, G. L., Wexler, R. R., Hobbs, F. W., and Olson, R. E. (1998) MEK inhibitors: the chemistry and biological activity of U0126, its analogs, and cyclization products, Bioorg. Med. Chem. Lett. 8, 2839-2844.
41. Mak, K. M., Wen, K., Ren, C., and Lieber, C. S. (2003) Dilinoleoylphosphatidylcholine reproduces the antiapoptotic actions of polyenylphosphatidylcholine against ethanol-induced hepatocyte apoptosis, Alcohol Clin. Exp. Res. 27, 997-1005.
42. Goedert, M., Sisodia, S. S., and Price, D. L. (1991) Neurofibrillary tangles and beta-amyloid deposits in Alzheimer's disease, Curr. Opin. Neurobiol. 1, 441-447.
43. Goedert, M., Spillantini, M. G., and Crowther, R. A. (1991) Tau proteins and neurofibrillary degeneration, Brain Pathol. 1, 279-286.
44. Guise, S., Braguer, D., Caries, G., Delacourte, A., and Briand, C. (2001) Hyperphosphorylation of tau is mediated by ERK activation during anticancer drug-induced apoptosis in neuroblastoma cells, J. Neurosci. Res. 63, 257-267.
45. Gomez-Ramos, A., Smith, M. A., Perry, G., and Avila, J. (2004) Tau phosphorylation and assembly, Acta Neurobiol. Exp. (Wars.) 64, 33-39.
46. Kayed, R., Head, E., Thompson, J. L., McIntire, T. M., Milton, S. C., Cotman, C. W., and Glabe, C. G. (2003) Common structure of soluble amyloid oligomers implies common mechanism of pathogenesis, Science 300, 486-489.
47. Shankar, G. M., Li, S., Mehta, T. H., Garcia-Munoz, A., Shepardson, N. E., Smith, I., Brett, F. M., Farrell, M. A., Rowan, M. J., Lernere, C. A., Regan, C. M., Walsh, D. M., Sabatini, B. L., and Selkoe, D. J. (2008) Amyloid-beta protein dimers isolated directly from Alzheimer's brains impair synaptic plasticity and memory, Nat. Med. 14, 837-842.
48. Irvine, G. B., El-Agnaf, O. M., Shankar, G. M., and Walsh, D. M. (2008) Protein aggregation in the brain: the molecular basis for Alzheimer's and Parkinson's diseases, Mol. Med. 14, 451-464.
49. Furukawa, K., Sopher, B. L., Rydel, R. E., Begley, J. G., Pham, D. G., Martin, G. M., Fox, M., and Mattson, M. P. (1996) Increased activity-regulating and neuroprotective efficacy of alpha-secretase-derived secreted amyloid precursor protein conferred by a C-terminal heparin-binding domain, J. Neurochem. 67, 1882-1896.
50. Combs, C. K., Karlo, J. C., Kao, S. C., and Landreth, G. E. (2001) beta-Amyloid stimulation of microglia and monocytes results in TNFalpha-dependent expression of inducible nitric oxide synthase and neuronal apoptosis, J. Neurosci. 21, 1179-1188.
51. Combs, C. K., Bates, P., Karlo, J. C., and Landreth, G. E. (2001) Regulation of beta-amyloid stimulated proinflammatory responses by peroxisome proliferator-activated receptor alpha, Neurochem. Int. 39, 449-457.
52. Walsh, D. M., Klyubin, I., Shankar, G. M., Townsend, M., Fadeeva, J. V., Betts, V., Podlisny, M. B., Cleary, J. P., Ashe, K. H., Rowan, M. J., and Selkoe, D. J. (2005) The role of cell-derived oligomers of Abeta in Alzheimer's disease and avenues for therapeutic intervention, Biochem. Soc. Trans. 33, 1087-1090.
53. Yin, Y. I., Bassit, B., Zhu, L., Yang, X., Wang, C., and Li, Y. M. (2007) {gamma}-Secretase Substrate Concentration Modulates the Abeta42/Abeta40 Ratio: IMPLICATIONS FOR ALZHEIMER DISEASE, J. Biol. Chem. 282, 23639-23644.
54. Farooqui, A. A., Hirashima, Y., and Horrocks, L. A. (1992) Brain phospholipases and their role in signal transduction, Adv. Exp. Med. Biol. 318, 11-25.
55. Farooqui, A. A., Ong, W. Y., and Horrocks, L. A. (2004) Biochemical aspects of neurodegeneration in human brain: involvement of neural membrane phospholipids and phospholipases A2, Neurochem. Res. 29, 1961-1977.
56. Bazan, N. G. (2005) Synaptic signaling by lipids in the life and death of neurons, Mol. Neurobiol. 31, 219-230.
57. Soderberg, M., Edlund, C., Kristensson, K., and Dallner, G. (1991) Fatty acid composition of brain phospholipids in aging and in Alzheimer's disease, Lipids 26, 421-425.
58. Nitsch, R. M., Blusztajn, J. K., Pittas, A. G., Slack, B. E., Growdon, J. H., and Wurtman, R. J. (1992) Evidence for a membrane defect in Alzheimer disease brain, Proc. Natl. Acad. Sci. U.S. A 89, 1671-1675.
59. Wells, K., Farooqui, A. A., Liss, L., and Horrocks, L. A. (1995) Neural membrane phospholipids in Alzheimer disease, Neurochem. Res. 20, 1329-1333.
60. Pettegrew, J. W., Panchalingam, K., Hamilton, R. L., and McClure, R. J. (2001) Brain membrane phospholipid alterations in Alzheimer's disease, Neurochem. Res. 26, 771-782.
61. Connor, W. E., Neuringer, M., and Lin, D. S. (1990) Dietary effects on brain fatty acid composition: the reversibility of n-3 fatty acid deficiency and turnover of docosahexaenoic acid in the brain, erythrocytes, and plasma of rhesus monkeys, J. Lipid Res. 31, 237-247.
62. Fenton, W. S., Hibbeln, J., and Knable, M. (2000) Essential fatty acids, lipid membrane abnormalities, and the diagnosis and treatment of schizophrenia, Biol. Psychiatry 47, 8-21.
63. Sumiyoshi, T., Matsui, M., Itoh, H., Higuchi, Y., Arai, H., Takamiya, C., and Kurachi, M. (2008) Essential polyunsaturated fatty acids and social cognition in schizophrenia, Psychiatry Res. 157, 87-93.

What is claimed is:

1. A method of inhibiting an accumulation of amyloid proteins, tau proteins or both proteins in neuronal cells comprising treating said neuronal cells with a composition comprising a linoleic phospholipid.

2. The method of claim 1, wherein the linoleic phospholipid is dilinoleoylphosphatidylcholine.

3. The method of claim 1, wherein the accumulation of amyloid protein is inhibited.

4. The method of claim 1, wherein the accumulation of tau protein is inhibited.

* * * * *